(12) United States Patent
Nakamura

(10) Patent No.: US 11,089,918 B2
(45) Date of Patent: Aug. 17, 2021

(54) PORTABLE CONTAINER

(71) Applicant: Tokue Inc., Nagoya (JP)

(72) Inventor: Saburo Nakamura, Chiryu (JP)

(73) Assignee: Tokue Inc., Nagoya (JP)

( * ) Notice: Subject to any disclaimer, the term of this patent is extended or adjusted under 35 U.S.C. 154(b) by 618 days.

(21) Appl. No.: 16/070,629

(22) PCT Filed: Feb. 9, 2017

(86) PCT No.: PCT/JP2017/004757
§ 371 (c)(1),
(2) Date: Jul. 17, 2018

(87) PCT Pub. No.: WO2017/138615
PCT Pub. Date: Aug. 17, 2017

(65) Prior Publication Data
US 2021/0204761 A1 Jul. 8, 2021

(30) Foreign Application Priority Data

Feb. 12, 2016 (JP) .............................. JP2016-025238

(51) Int. Cl.
*B65D 83/00* (2006.01)
*A47K 7/08* (2006.01)
*B05C 17/005* (2006.01)

(52) U.S. Cl.
CPC .............. *A47K 7/08* (2013.01); *B05C 17/005* (2013.01); *B65D 83/0055* (2013.01)

(58) Field of Classification Search
CPC ...... B65D 83/0055; B05C 17/005; A47K 7/08
(Continued)

(56) References Cited

U.S. PATENT DOCUMENTS

2004/0082924 A1* 4/2004 Moser ..................... A47K 7/08
604/279
2004/0216224 A1* 11/2004 Smith .................... E03D 9/085
4/443
(Continued)

FOREIGN PATENT DOCUMENTS

CN           2499041 Y      7/2002
CN         102218181 A     10/2011
(Continued)

OTHER PUBLICATIONS

International Search Report dated May 9, 2017, issued for PCT/JP2017/004757.
(Continued)

*Primary Examiner* — Jeremy Carroll
(74) *Attorney, Agent, or Firm* — Locke Lord LLP

(57) ABSTRACT

Provided is a portable bidet capable of maintaining the quality of cleaning water. A portable bidet is configured to include a tank portion formed to be compression-deformable and restorable to its original shape, a nozzle that is connected to the tank portion and can discharge a fluid, and a sealing portion that is provided continuously to the nozzle. The tank portion and the nozzle are connected via a cylindrical portion having a cylindrical shape. In a sealed state where the fluid is sealed by the sealing portion, the fluid is fully filled in a storing chamber in a state where the tank portion is compressed, and in an opened state where sealing by the sealing portion is released, the tank portion is restored to its original shape, and a volume of the storing chamber is expanded as compared with a volume of the storing chamber in the sealed state.

1 Claim, 16 Drawing Sheets

(58) Field of Classification Search
USPC .............................................................. 4/443
See application file for complete search history.

(56) References Cited

U.S. PATENT DOCUMENTS

| | | | |
|---|---|---|---|
| 2006/0180183 A1* | 8/2006 | Yu ............................ | A47K 7/08 |
| | | | 134/41 |
| 2008/0054024 A1 | 3/2008 | Kubota | |
| 2008/0067194 A1 | 3/2008 | Faurie | |
| 2011/0253805 A1 | 10/2011 | Lee | |
| 2014/0209639 A1 | 7/2014 | Sasaki et al. | |
| 2016/0177555 A1* | 6/2016 | Yousif ..................... | E03D 9/085 |
| | | | 4/443 |
| 2018/0010324 A1* | 1/2018 | Culton, Sr. ......... | A61M 3/0262 |
| 2019/0104893 A1* | 4/2019 | DeBlasi .............. | A61M 3/0279 |

FOREIGN PATENT DOCUMENTS

| | | |
|---|---|---|
| CN | 103764517 A | 4/2014 |
| CN | 105059647 A | 11/2015 |
| JP | 62-064549 U | 4/1987 |
| JP | 63-130050 U | 8/1988 |
| JP | 10-211115 A | 8/1998 |
| JP | 11-70057 A | 3/1999 |
| JP | 2003-190248 A | 7/2003 |
| JP | 3121983 U | 6/2006 |
| JP | 2007307317 A | 11/2007 |
| JP | 2013-256300 A | 12/2013 |
| JP | 2015-063315 A | 4/2015 |
| WO | 2006/00897 A1 | 1/2006 |
| WO | 2006/038604 A1 | 4/2006 |
| WO | 2006/116389 A2 | 11/2006 |

OTHER PUBLICATIONS

Search Report dated Mar. 30, 2020, issued for the Chinese Patent Application No. 2017800109044.
Search Report dated Mar. 30, 2020, issued for the Taiwanese Patent Application No. 2017800109044.

* cited by examiner

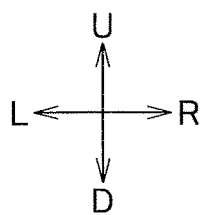
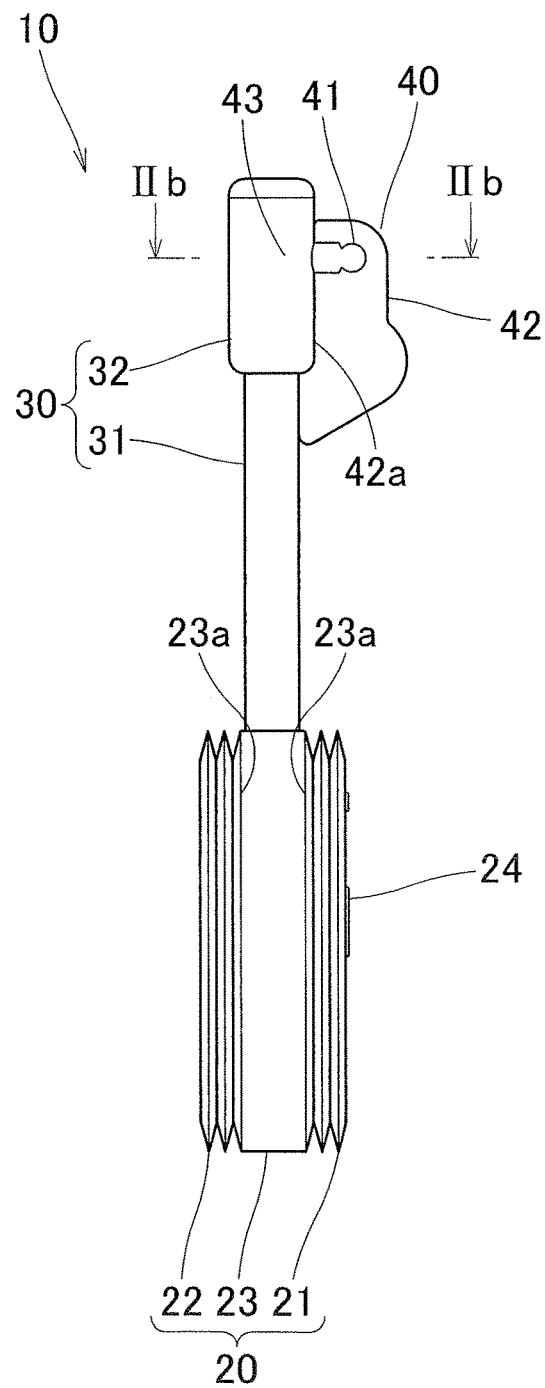
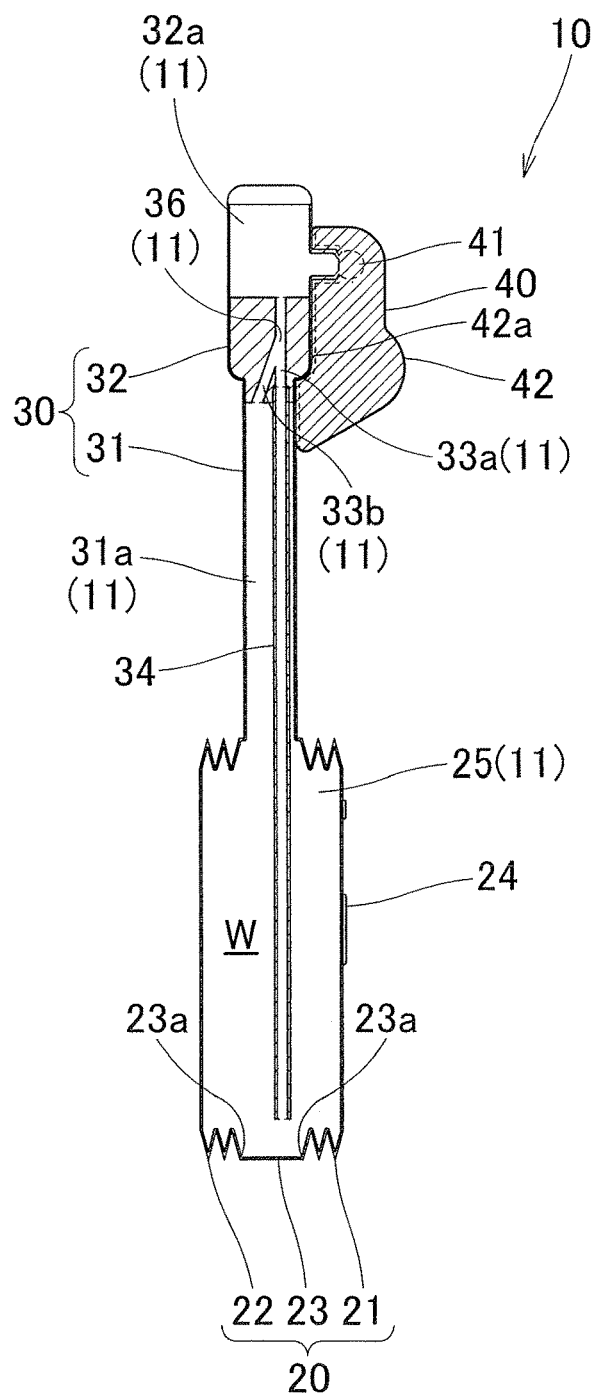
FIG. 1(a)  FIG. 1(b)

F I G . 11(a)
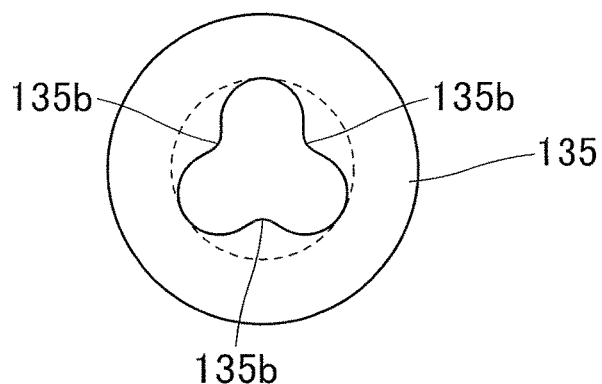
F I G . 11(b)
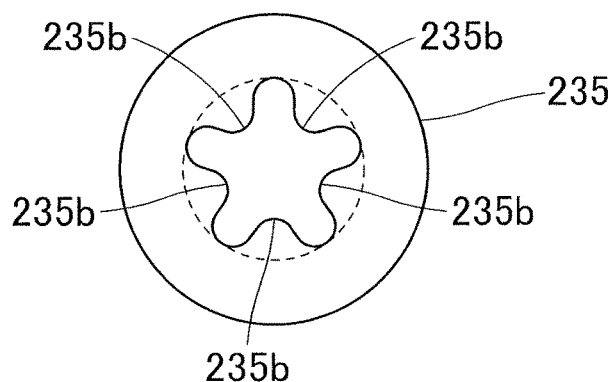
F I G . 11(c)
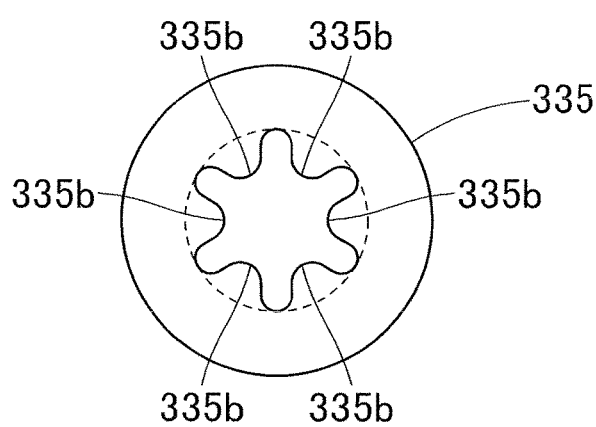
F I G . 11(d)
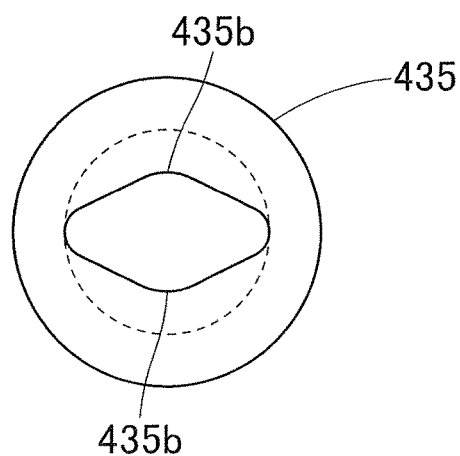

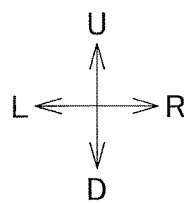
FIG.12(a)
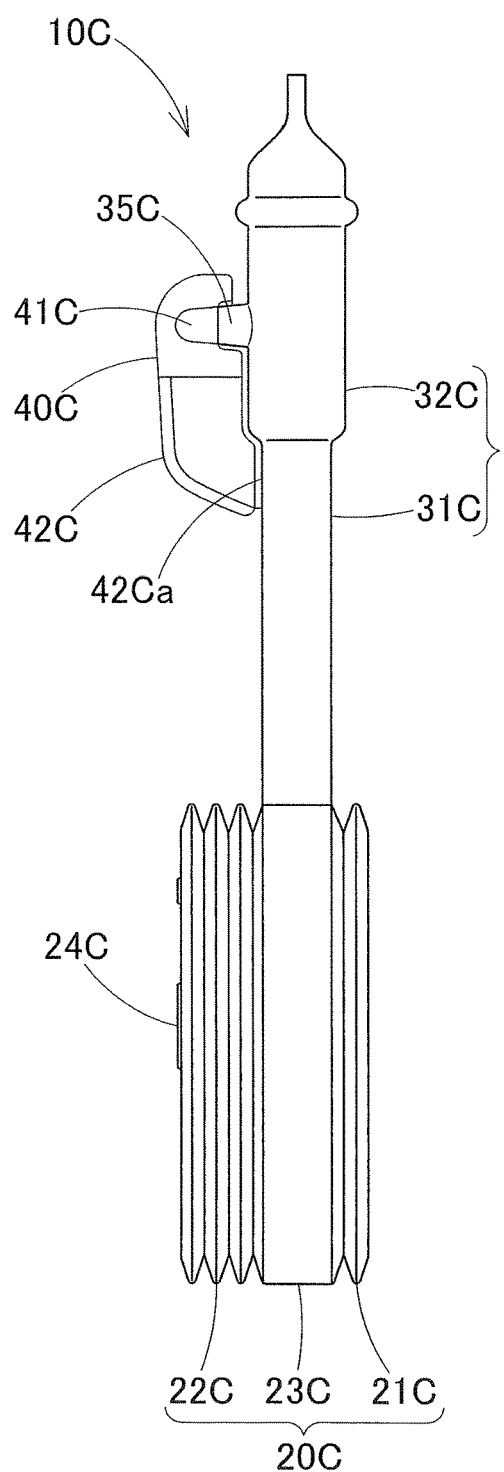
FIG.12(b)
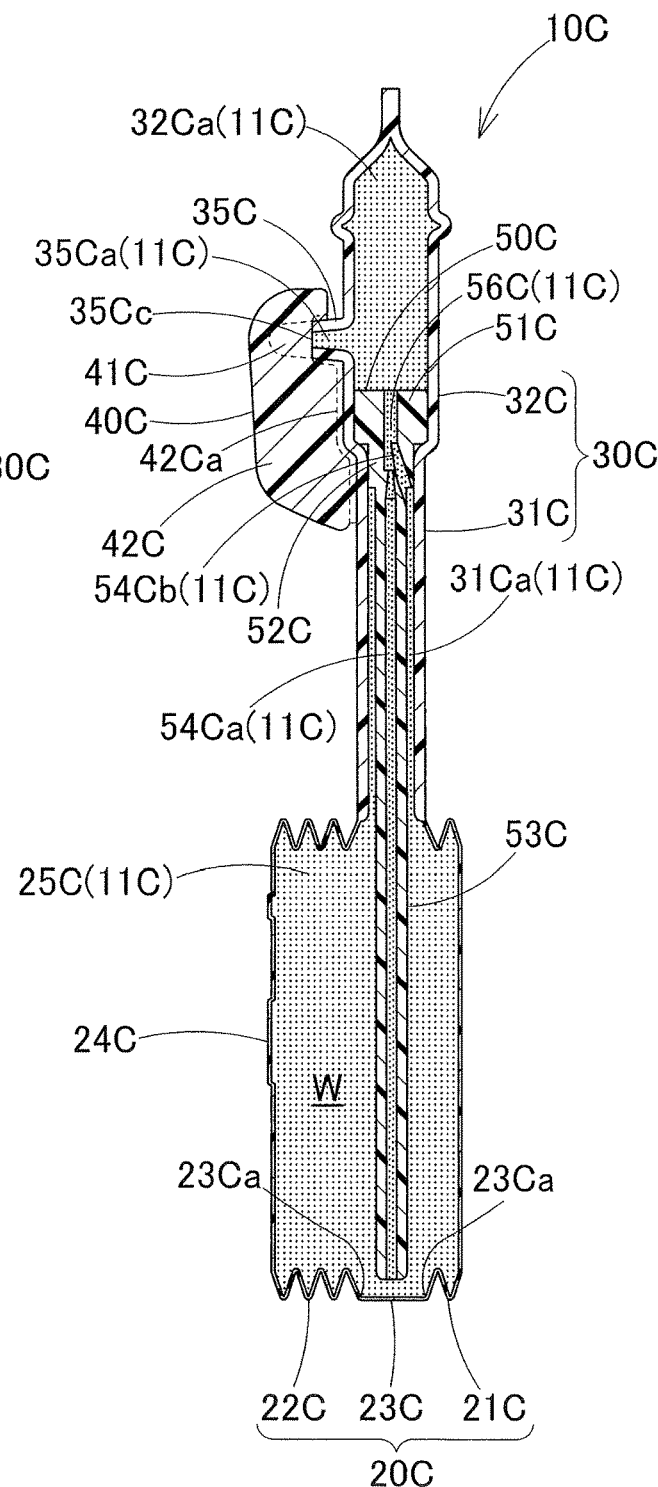

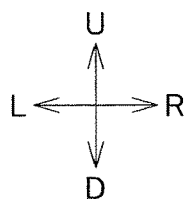
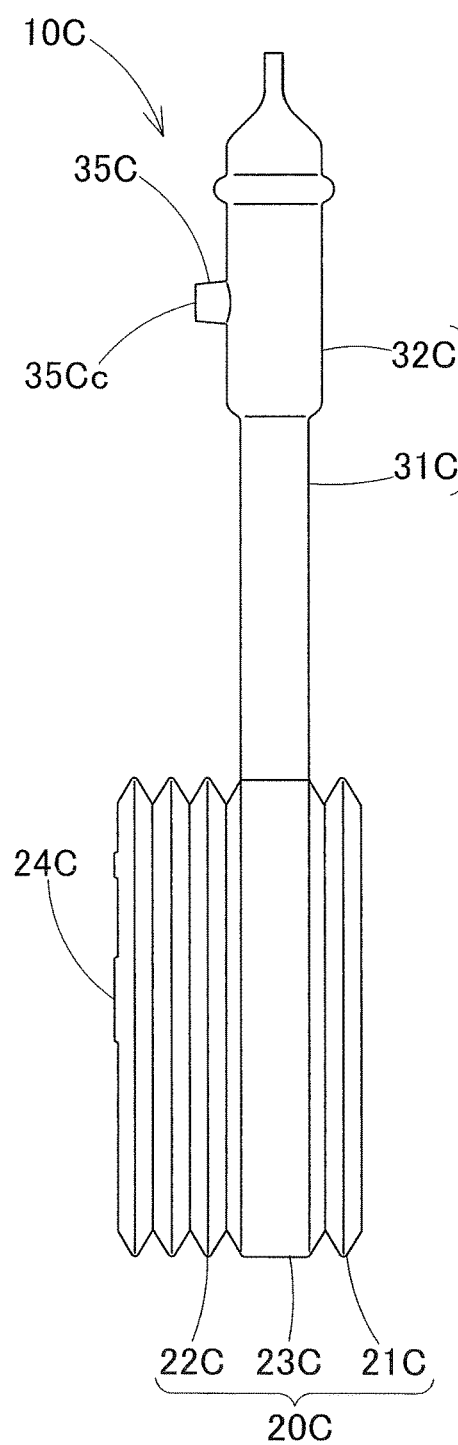
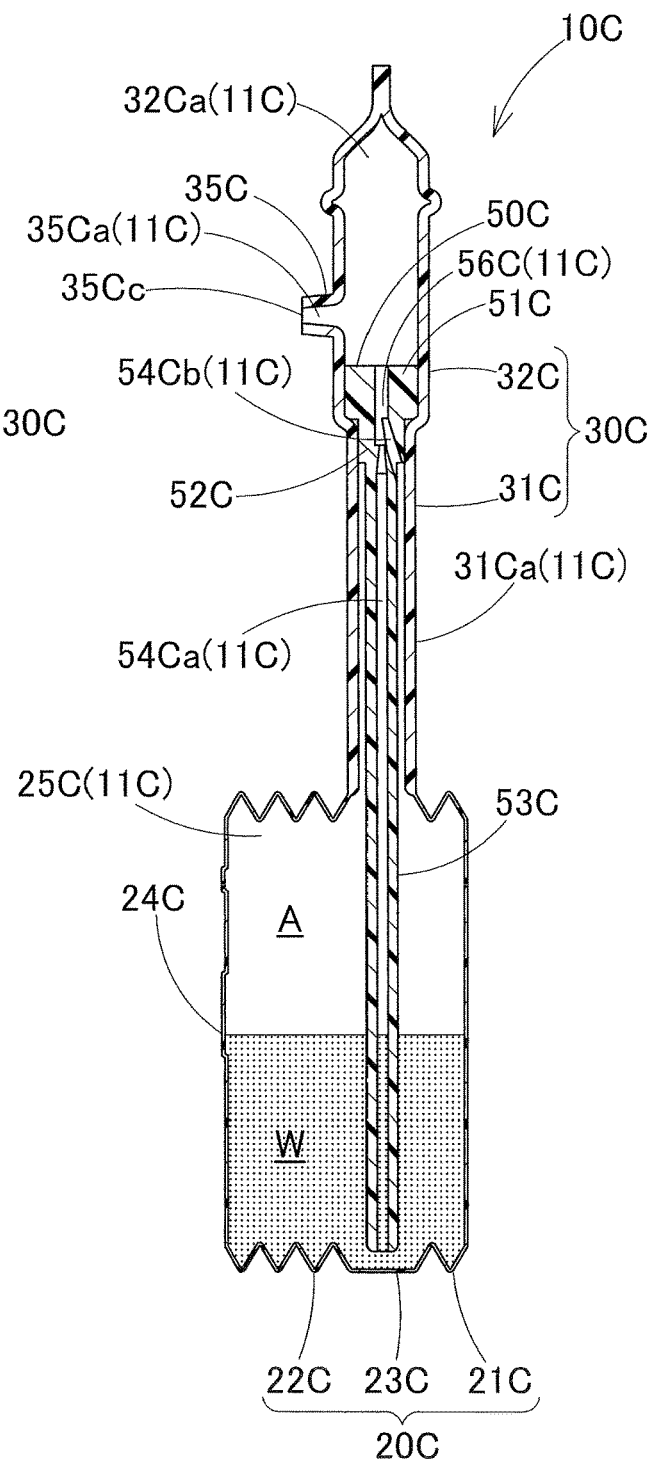
FIG. 13(a)
FIG. 13(b)

F I G. 14(a)
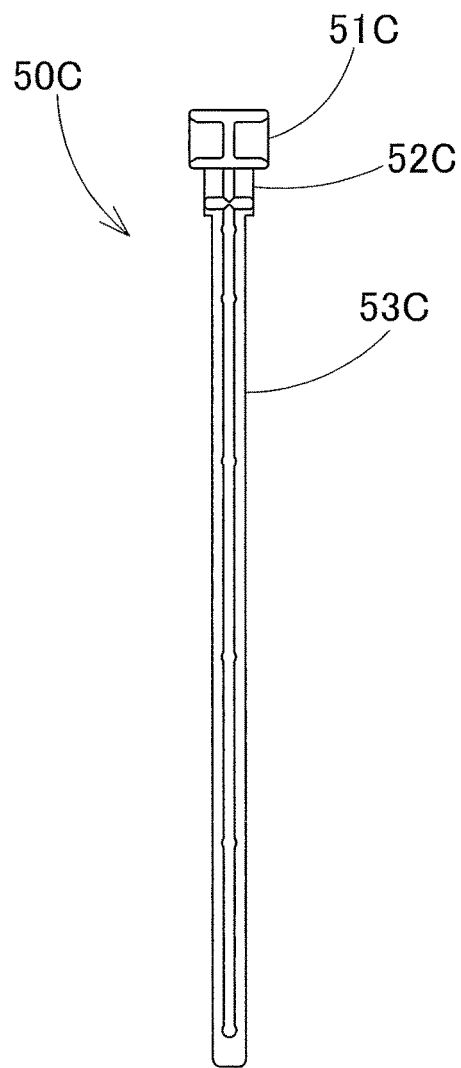
F I G. 14(b)
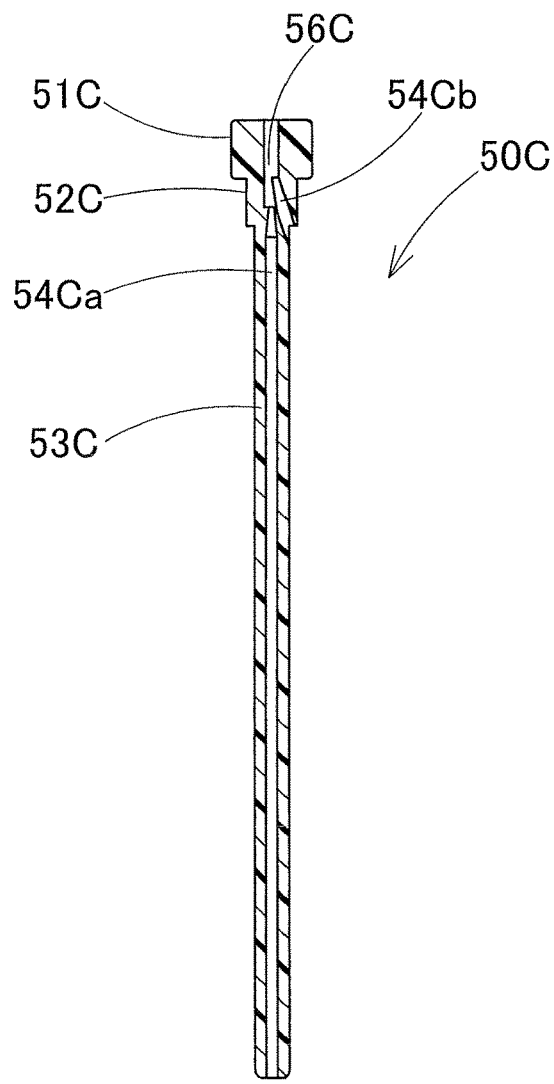
F I G. 14(c)
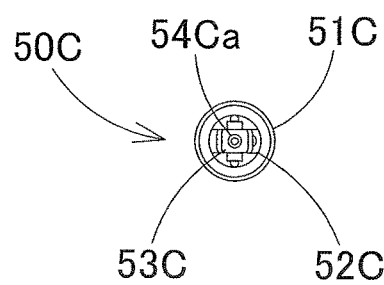

F I G. 16(a)　　F I G. 16(b)　　F I G. 16(c)
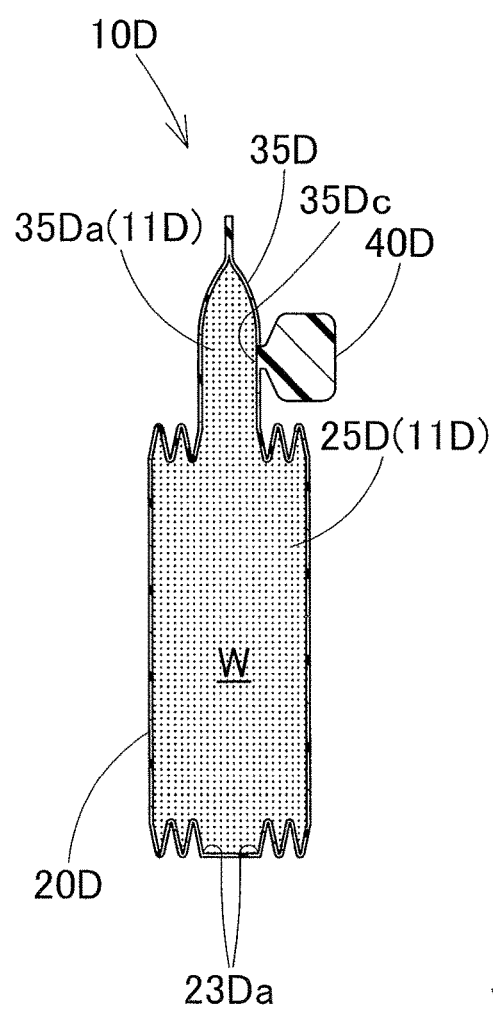
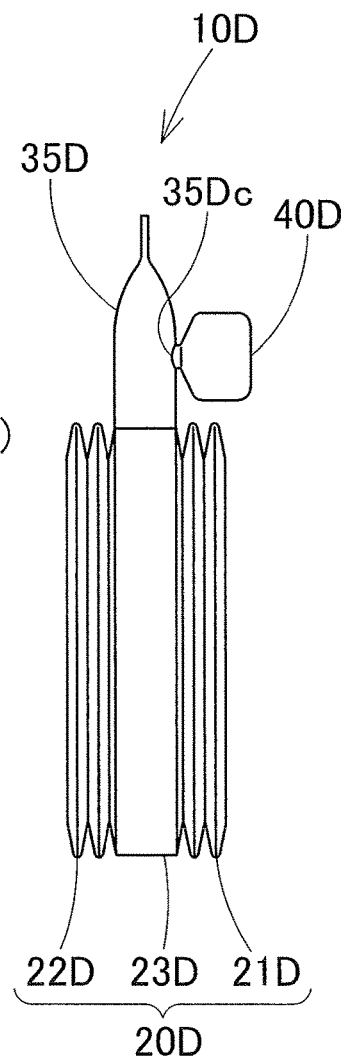
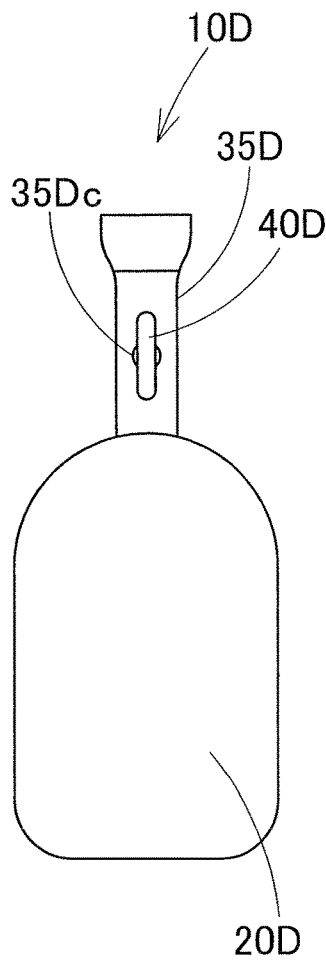

PORTABLE CONTAINER

TECHNICAL FIELD

The present invention relates to a portable container capable of jetting (discharging) a fluid.

BACKGROUND ART

Patent Literature 1 describes a portable bidet including a main body having a bellows structure that can store cleaning water and can freely expand and contract, and a beak portion having a waterjet orifice disposed on one end side in an expansion/contraction direction.

The main body and the beak portion are coupled to each other by a screw cap (screw type), and at the time of use, the beak portion is removed in advance from the main body portion and cleaning water is injected, and the beak portion is attached again, and thereafter, the main body is pressed to jet the cleaning water stored inside to clean contamination on a cleaning portion.

CITATION LIST

Patent Literature

Patent Literature 1: JP 2007-307317A

SUMMARY OF INVENTION

Technical Problem

However, the portable bidet described above has problems in which repetition of injection of cleaning water causes the inside of the main body to be contaminated, and when tap water is injected as cleaning water in a region in a poor plumbing environment, the cleaning water itself to be injected may be contaminated. In addition, there is a problem that when injected cleaning water inside the main body comes into contact with air, the cleaning water degrades, and the quality of the cleaning water cannot be maintained.

In view of the above, an object of the present invention is to provide a portable container capable of maintaining the quality of a fluid (cleaning water).

Solution to Problem

In an invention described in claim 1, a portable container includes a tank portion formed to be compression-deformable and restorable to its original shape, a nozzle that is connected to the tank portion and can discharge a fluid, and a sealing portion that is provided continuously to the nozzle and can seal the fluid, and has a storing chamber in which the fluid is stored, disposed at least in the tank portion and the nozzle, wherein the portable container is configured so that, in a sealed state where the fluid is sealed by the sealing portion, the fluid is fully filled in the storing chamber in a state where the tank portion is compressed, and in an opened state where sealing by the sealing portion is released, the tank portion is restored to its original shape, and a volume of the storing chamber is expanded as compared with a volume of the storing chamber in the sealed state.

With this configuration, at the time of nonuse, the quality of the fluid is maintained in a sealed state where it does not come into contact with air, and at the time of use, the state is changed into an opened state and air is taken into the storing chamber to restore the tank portion to its original shape so that the volume of the storing chamber is expanded as compared with a volume of the storing chamber in the sealed state, making it possible to press the fluid by the taken-in air, and accordingly the fluid can be properly discharged. When the sealing portion is opened, air enters from the opened portion, and the fluid is pressed into the storing chamber, so that the fluid filled in the storing chamber of the portable container does not spurt out, and therefore, the container can be used without getting hands wet.

By adopting a configuration in which the tank portion and the nozzle are connected via a cylindrical portion having a cylindrical shape, a hand to compress the tank portion and a portion to which a fluid is discharged can be kept away from each other, and the discharged fluid and contamination, etc., can be suppressed from adhering to hands.

In addition, the fluid is a liquid, an air passage through which air is distributed and a liquid passage through which the liquid is distributed are disposed in the cylindrical portion, the air passage and the liquid passage are formed to join together, and when discharging the liquid, by compressing the tank portion, the air distributed through the air passage and the liquid distributed through the liquid passage join together, and a mixed fluid of the air and the liquid granulated is discharged to the outside.

With this configuration, by discharging a mixed fluid of the air and the granulated liquid, it is possible to soften the contact of the liquid, and the portable container can be used even when a portion to which the liquid is discharged is diseased. By granulating the liquid, the usage of the liquid can be reduced in amount as compared with a case of discharging in a liquid state.

A passage forming member having the air passage and the liquid passage is fitted to the inside of the cylindrical portion.

With this configuration, by a simple operation of fitting the passage forming member to the inside of the cylindrical portion, the air passage and the liquid passage can be provided in the portable container, so that the number of manufacturing steps and the manufacturing cost can be reduced.

In a case where a chamber in which the mixed fluid is stirred is disposed between a junction portion of the air passage and the cleaning water passage and the nozzle, by stirring the mixed fluid, it is possible to soften the contact of the cleaning water with a cleaning portion as compared with the case where the mixed fluid is directly jetted from the junction portion of the air passage and the cleaning water passage. Further, a portion surrounded by the passage forming member and the cylindrical portion is provided as a chamber.

BRIEF DESCRIPTION OF DRAWINGS

FIG. 1(*a*) is a front view and FIG. 1(*b*) is a sectional front view, showing a sealed state of a portable bidet according to a first embodiment of the present invention.

FIG. 11 are enlarged side views showing modifications of flow regulation portions.

FIG. 12(a) is a front view and FIG. 12(b) is a sectional front view, showing a sealed state of a portable bidet according to a fourth embodiment of the present invention.

FIG. 13(a) is a front view and FIG. 13(b) is a sectional front view, showing an opened state of the portable bidet according to the fourth embodiment of the present invention.

FIG. 14(a) is a front view, FIG. 14(b) is a sectional front view, and FIG. 14(c) is a bottom view, showing a passage forming member in the fourth embodiment of the present invention.

FIG. 16(a) is a sectional front view, FIG. 16(b) is a front view, and FIG. 16(c) is a right side view, showing a sealed state of a portable bidet according to a fifth embodiment of the present invention.

DESCRIPTION OF EMBODIMENTS

Hereinafter, an embodiment of the present invention is described with reference to the drawings. In the following description, of the arrows in each drawing, the arrow F denotes the front side, the arrow B denotes the rear side, the arrow R denotes the right side, the arrow L denotes the left side, the arrow U denotes the upper side, and the arrow D denotes the lower side.

In the present embodiment, a disposable portable bidet 10 as a portable container capable of cleaning the buttocks is described. As shown in FIG. 1 to FIG. 5, the portable bidet 10 is made of polyethylene, and includes a tank portion 20, a jet tube portion 30, and a sealing portion 40.

Figure 3A:
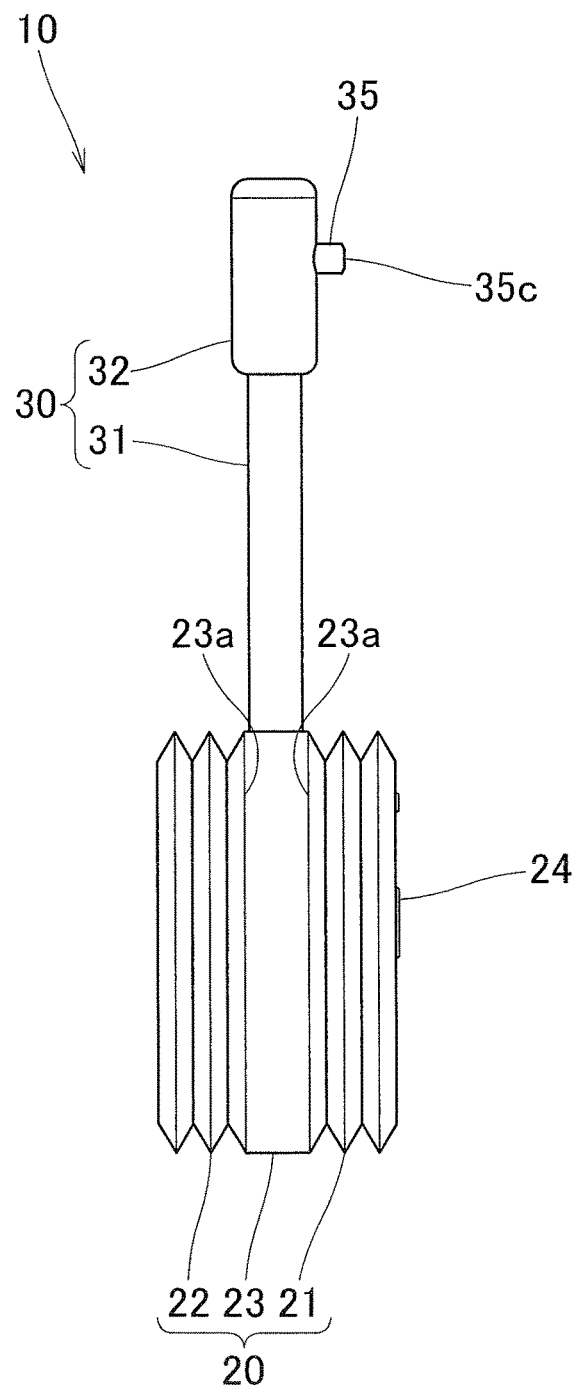
FIG. 3(*a*) is a front view and FIG. 3(*b*) is a sectional front view, showing an opened state of the portable bidet according to the first embodiment of the present invention.
Figure 3B:
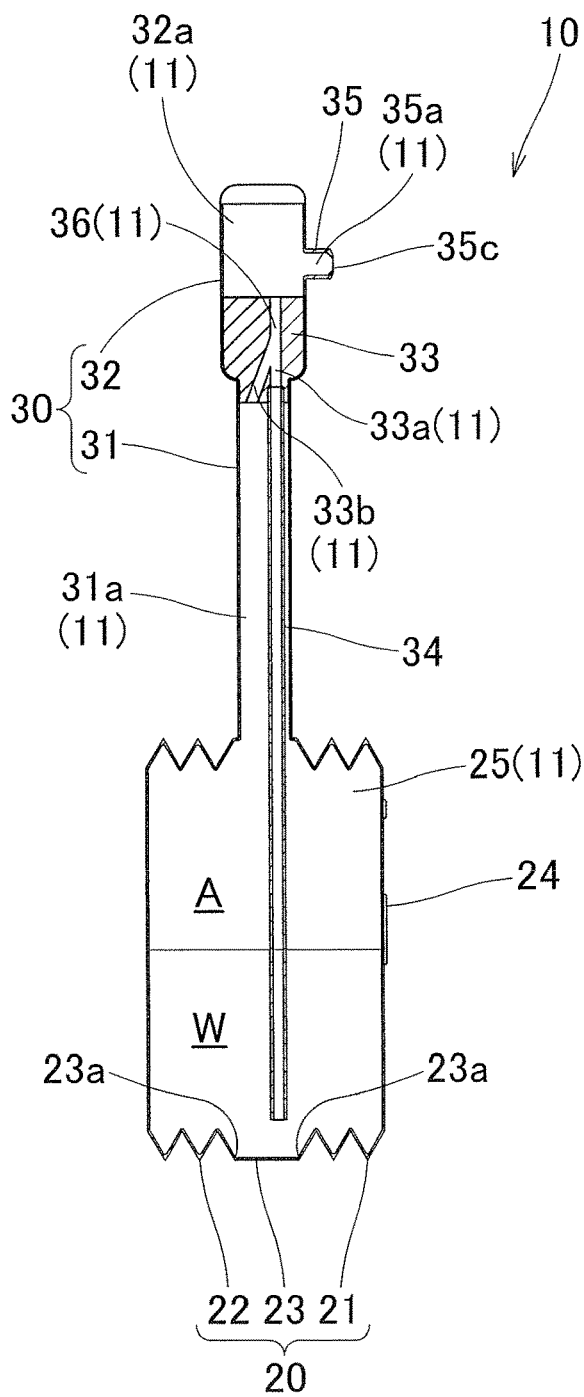
Figure 4:
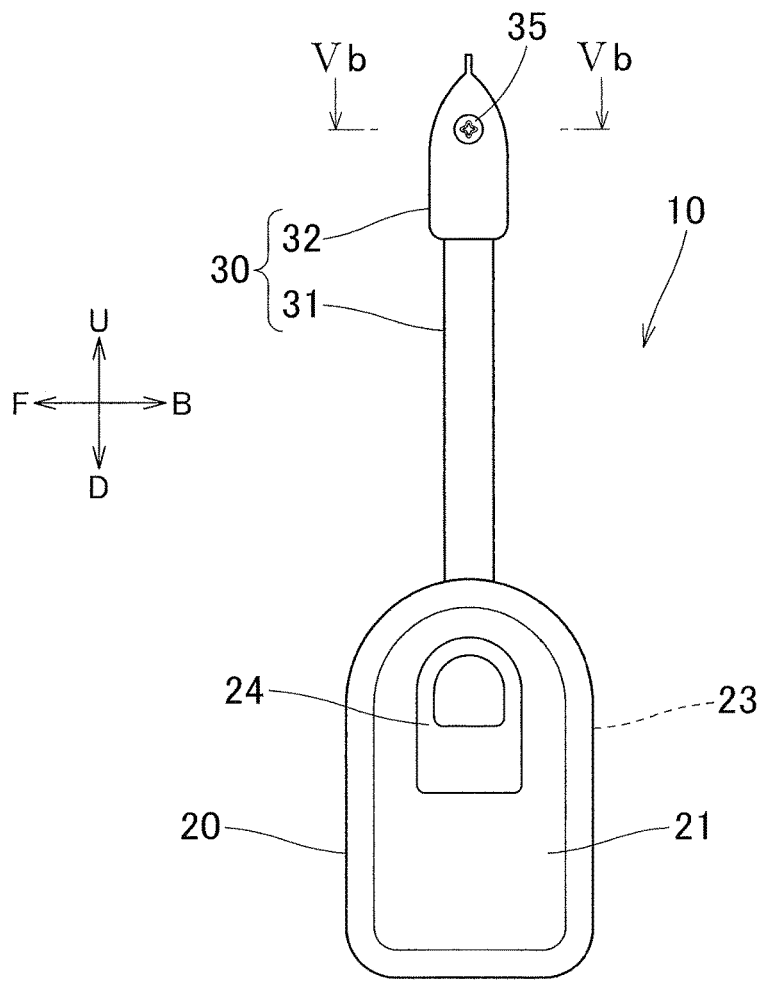
FIG. 4 is a right side view of the portable bidet according to the first embodiment of the present invention.

As shown in FIGS. 1, 3, and 4, the tank portion 20 has a hollow bellows structure that includes a pair of bellows portions 21 and 22 and an expansion/contraction restricting portion 23 that is disposed between the pair of bellows portions 21 and 22 and restricts compression of the bellows portions 21 and 22 in an expansion/contraction direction, and can store cleaning water W (pure water) as a fluid inside, and is formed to be compression-deformable and restorable to its original shape in the left-right direction (expansion/contraction direction).

In the present embodiment, the number of mountain fold portions that the bellows of each of the bellows portions 21 and 22 has is set to two.

On a right side wall of the bellows portion 21, as shown in FIGS. 1, 3, and 4, a projection portion 24 annularly projecting rightward is disposed. The projection portion 24 projects in the same direction as a jetting direction of a nozzle 35 described below so that, at the time of use, by touching the projection portion 24 by hand, a user can feel a jetting direction of cleaning water W without viewing it directly.

The expansion/contraction restricting portion 23 is formed into a cylindrical shape that has a substantially U-shaped lower side and a substantially semicircular arc-shaped upper side as viewed in the left-right direction and is opened in the left-right direction. As can be referred to in FIG. 6, when the bellows portions 21 and 22 are compressed, opening edge portions 23a and 23a in the left-right direction of the expansion/contraction restricting portion 23 come into contact with the bellows portions 21 and 22 to restrict excessive compression of the bellows portions 21 and 22 in the left-right direction (expansion/contraction direction).

A space portion inside the tank portion 20 is provided as a tank storing chamber 25 constituting a part of a storing chamber 11 through which cleaning water W is stored.

The jet tube portion 30 includes a neck portion 31 and a head portion 32, and is connected to the tank portion 20 to become capable of jetting the cleaning water W.

The neck portion 31 is formed into a circular cylindrical shape. A space portion inside the neck portion 31 is provided as a neck portion storing chamber 31a constituting a part of the storing chamber 11 in which the cleaning water W is stored. In the neck portion 31, by the tank storing chamber 25 and the neck portion storing chamber 31a communicating with each other, a lower end of the neck portion 31 is connected to the expansion/contraction restricting portion 23.

The head portion 32 is formed into a circular cylindrical shape with a larger diameter than the neck portion 31 having a space portion, and an upper end thereof is sandwiched together in a front-rear direction so that an upper portion becomes gradually narrower upward as viewed in the left-right direction.

Around a boundary portion between the neck portion 31 and the head portion 32, a solid portion 33 formed to be solid is disposed. In the solid portion 33, an air passage 33a through which air A is distributed and a cleaning water passage 33b through which the cleaning water W is distributed are disposed. The passages are formed such that the cleaning water passage 33b extending from the diagonally lower left side joins toward the air passage 33a extending along a substantially up-down direction. The portion at which the air passage 33a and the cleaning water passage 33b join together is provided as a junction portion 36.

To a lower end portion of the air passage 33a, a circular cylindrical air distribution tube 34 is fitted. The air distribution tube 34 is disposed to enter the inside of the tank portion 20. The inside of the air distribution tube 34 constitutes a part of the air passage 33a through which air A is distributed.

The air distribution tube 34 is, in the present embodiment, set to 95% of an inside dimension of the tank portion 20 in the up-down direction, however, it can be properly set in a range of 80 to 95% of the inside dimension of the tank portion 20 in the up-down direction.

In a space portion of the head portion 32, a portion surrounded by an upper surface of the solid portion 33 and an inner surface of the head portion 32 is provided as a chamber 32a. In the chamber 32a, a mixed fluid MF of the air A and granulated cleaning water GW described below is stirred. The chamber 32a constitutes a part of the storing chamber 11 in which the cleaning water W is stored.

On a right side wall of the chamber 32a, a nozzle 35 capable of jetting the cleaning water W is disposed. The nozzle 35 is formed into a substantially truncated cone shape having a hollow mixed fluid passage 35a. The mixed fluid passage 35a constitutes a part of the storing chamber 11 in which the cleaning water W is stored.

The chamber 32a in which the mixed fluid MF is stirred is disposed between the junction portion 36 of the air passage 33a and the cleaning water passage 33b and the nozzle 35.

Figures 5A, 5B:
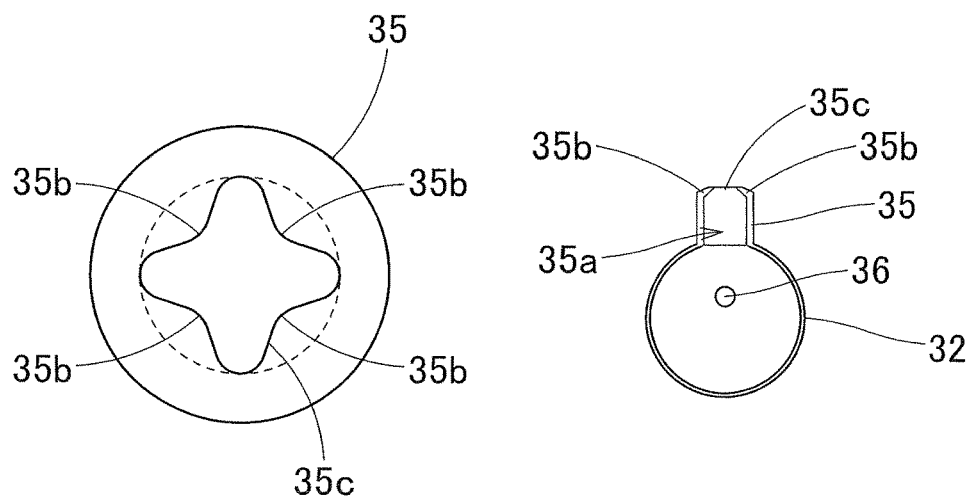
FIG. 5(a) is a partially enlarged side view of a nozzle.
FIG. 5(b) is a sectional view taken in the direction of arrows along line Vb-Vb in FIG. 4.

In the nozzle 35, flow regulation portions 35b that restrict a jetting direction of the cleaning water W are disposed. In the present embodiment, each flow regulation portion 35b is formed into a mountain shape having an obtuse apex portion as viewed in the left-right direction as shown in FIGS. 5(a) and 5(b) so that, in an opened state, a jetting orifice 35c has a substantially cross shape as viewed from a side surface as shown in FIG. 5(a).

Figure 2A:
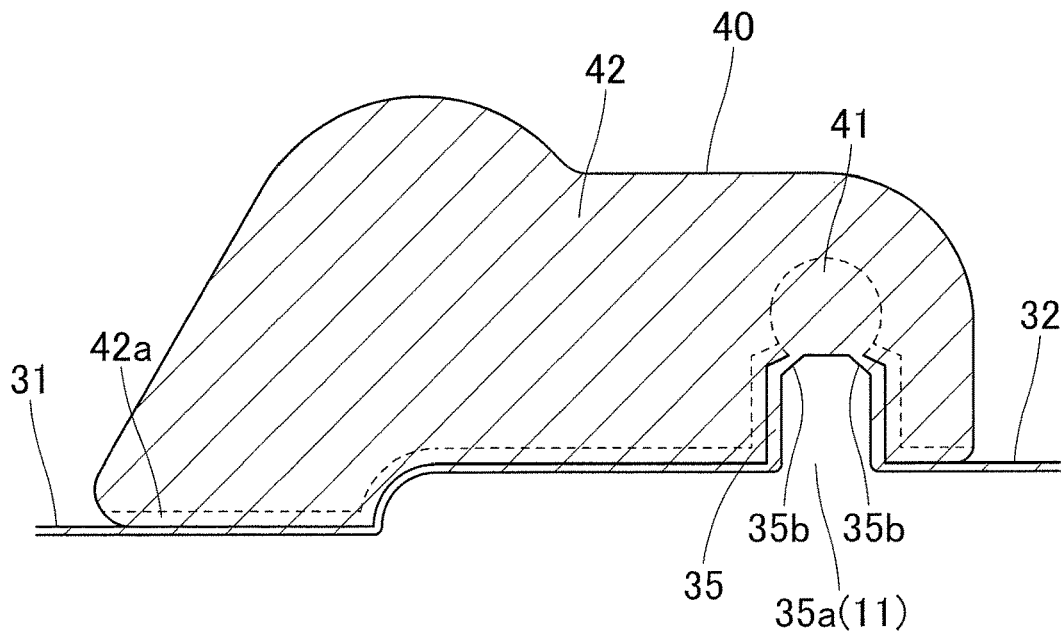
FIG. 2(*a*) is a partially enlarged sectional view of FIG. 1(*b*), and FIG. 2(*b*) is a sectional view taken in the direction of arrows along line in FIG. 1(*a*).
Figure 2B:
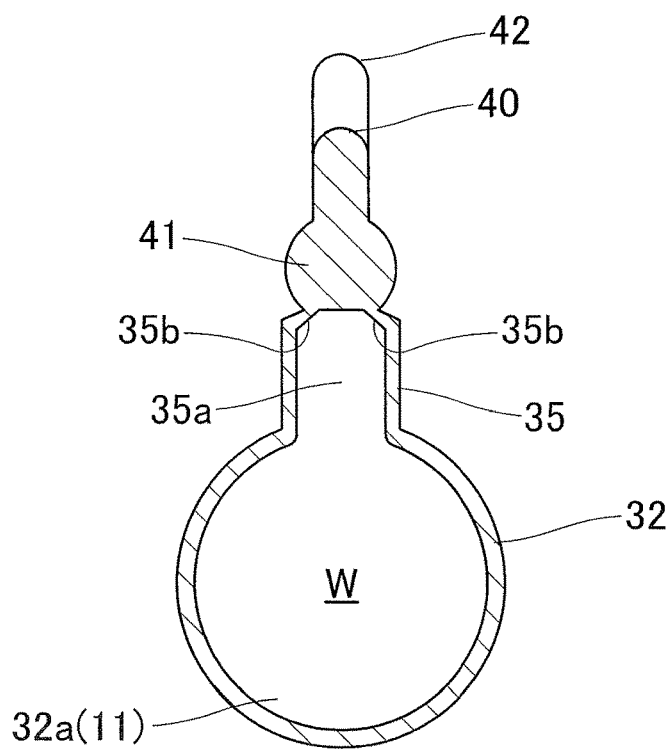

As shown in FIGS. 1 and 2, the sealing portion 40 includes an opening assist portion 41 and a holding margin portion 42, and is provided continuously to the neck portion 31, the head portion 32, and the nozzle 35.

The opening assist portion 41 is formed into a substantially spherical shape, and in a sealed state, blocks the mixed fluid passage 35a of the nozzle 35, and when opening, the opening assist portion 41 is separated from the nozzle 35 to securely form the jetting orifice 35c.

The holding margin portion 42 is formed into a substantially trapezoidal plate shape. At a boundary portion of the holding margin portion 42 with the neck portion 31 and head portion 32, a thinned portion 42a formed to be thinner in thickness than other portions of the holding margin portion 42 is disposed so that the sealing portion 40 is easily separated from the jet tube portion 30.

In a state where the portable bidet 10 is sealed, an internal space portion formed by the tank storing chamber 25 of the tank portion 20, the neck portion storing chamber 31a and the chamber 32a of the jet tube portion 30, the air passage 33a and the cleaning water passage 33b of the solid portion 33, the junction portion 36 of the air passage 33a and the cleaning water passage 33b, and the mixed fluid passage 35a of the nozzle 35 communicating with each other, is provided as the storing chamber 11 in which the cleaning water W is filled.

Figure 6:
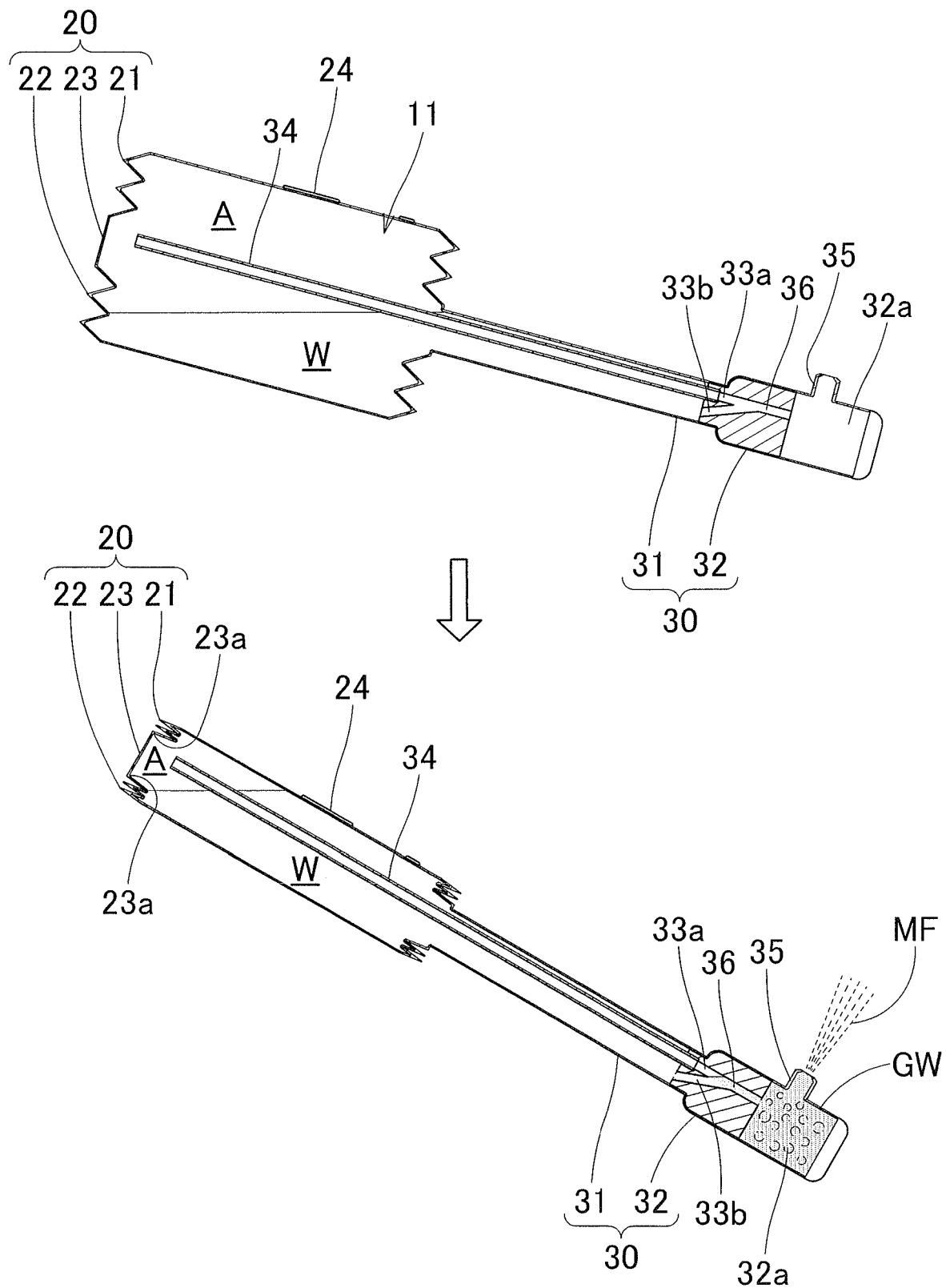
FIG. 6 is an explanatory view showing a usage state of the portable bidet.

In the present embodiment, in the sealed state shown in FIG. 1, a filling amount of the cleaning water W is 12.5 cc when fully filled, and in the usage state shown in FIG. 6, the volume of the storing chamber 11 is set to such an extent that the air distribution tube 34 is exposed from a liquid level of the cleaning water W.

Next, a usage mode of the portable bidet 10 of the embodiment described above is described. In FIG. 1, the cleaning water W is sealed by the sealing portion 40, and the tank portion 20 is in a compressed state. From the sealed state shown in FIG. 1, the holding margin portion 42 of the sealing portion 40 is held by hand, and torn off from the nozzle 35 and opened. At this time, when the opening assist portion 41 is separated and the jetting orifice 35c of the nozzle 35 is opened, air A enters from the jetting orifice 35c, so that the cleaning water W filled in the storing chamber 11 of the portable bidet 10 does not spurt out. Then, in the state shown in FIG. 3, the tank portion 20 is restored to its original shape.

Then, as shown in FIG. 6, the portable bidet is held by hand so that the jet tube portion 30 comes to the lower side. Since the projection portion 24 projects in the same direction (rightward) as the jetting direction of the nozzle 35, by touching the projection portion 24 by hand, a user can recognize the jetting direction of the nozzle 35, and the nozzle 35 is prevented from being turned to the opposite side of a cleaning portion.

Then, in the state shown in FIG. 6, the air distribution tube 34 is exposed from the liquid level of the cleaning water W, and when the pair of bellows portions 21 and 22 are compressed toward the expansion/contraction restricting portion 23, the tank portion 20 is compressed, and accordingly, air A is distributed inside the air distribution tube 34, that is, the air passage 33a, and the cleaning water W is distributed inside the cleaning water passage 33b.

Then, when jetting the cleaning water W, the air A distributed through the air passage 33a and the cleaning water W distributed through the cleaning water passage 33b join together at the junction portion 36 to become a mixed fluid MF of the air A and granulated cleaning water GW.

The mixed fluid MF flows into the chamber 32a and is stirred by colliding with an inner wall of the chamber 32a, and flows into the nozzle 35 disposed so as to jet the fluid in a direction different from the flowing-in direction. Then, the mixed fluid MF is jetted to the outside while being prevented from diffusing by the flow regulation portions 35b (refer to FIG. 5) formed inside the nozzle 35. The cleaning water W constituting the mixed fluid MF is granulated, so that contact thereof with the cleaning portion is softened.

In addition, compression in the expansion/contraction direction of the bellows portions 21 and 22 is restricted in compression by the opening edge portions 23a and 23a of the expansion/contraction restricting portion 23, and damage to the air distribution tube 34 is suppressed, and the mixed fluid MF (granulated cleaning water GW) is prevented from being more strongly jetted than necessary.

The portable bidet 10 as a portable container configured as described above includes the tank portion 20 formed to be compression-deformable and restorable to its original shape, the jet tube portion 30 that has the nozzle 35 and is connected to the tank portion 20 and can jet cleaning water W, and the sealing portion 40 that is connected to the jet tube portion 30 and can seal the cleaning water W, and has the storing chamber 11 in which the cleaning water W is stored and which is disposed at least in the tank portion 20 and the jet tube portion 30, and in a sealed state where the cleaning water W is sealed by the sealing portion 40, the cleaning water W is fully filled in the storing chamber 11 while the tank portion 20 is compressed, and in an opened state where sealing by the sealing portion 40 is released, the tank portion 20 is restored to its original shape, and a volume of the storing chamber 11 is expanded as compared with a volume of the storing chamber 11 in the sealed state.

With this configuration, at the time of nonuse, the quality of the cleaning water W is maintained in a sealed state where it does not come into contact with air A, and at the time of use, the state is changed into an opened state and air A is taken into the storing chamber 11 to restore the tank portion 20 to its original shape so that the volume of the storing chamber 11 is expanded as compared with a volume of the storing chamber 11 in the sealed state, making it possible to press the cleaning water W by the taken-in air A, and accordingly, the cleaning water W can be properly jetted to a cleaning portion. When the sealing portion 40 is opened, air A enters from the opened portion, and the cleaning water W is pressed into the storing chamber 11, so that the cleaning water W filled in the storing chamber 11 of the portable bidet 10 does not spurt out, and therefore, the portable bidet can be used without getting hands wet.

In the jet tube portion 30, an air passage 33a through which the air A is distributed and a cleaning water passage 33b through which the cleaning water W is distributed are disposed, the air passage 33a and the cleaning water passage 33b are formed to join together, and when jetting the cleaning water W, by compressing the tank portion 20, the air A distributed through the air passage 33a and the cleaning water W distributed through the cleaning water passage 33b join together, and a mixed fluid MF of the air A and the granulated cleaning water GW is jetted to the outside.

With this configuration, by jetting the mixed fluid MF of the air A and the granulated cleaning water GW, it is possible to soften the contact of the cleaning water W with a cleaning portion, so that the portable bidet can be used even when the cleaning portion is diseased. By granulating the cleaning water W, the usage of the cleaning water W can be reduced in mount as compared with the case where the cleaning water W in a liquid state is jetted.

In addition, the chamber 32a in which the mixed fluid MF is stirred is disposed between the junction portion 36 of the air passage 33a and the cleaning water passage 33b and the nozzle 35, so that by stirring the mixed fluid MF, it is possible to soften the contact of the cleaning water W with a cleaning portion as compared with the case where the mixed fluid MF is directly jetted from the junction portion 36 of the air passage 33a and the cleaning water passage 33b.

In addition, flow regulation portions 35b to regulate a jetting direction of the cleaning water W (mixed fluid MF) are disposed in the nozzle 35, so that the granulated cleaning water GW can be accurately jetted to a cleaning portion.

In addition, the tank portion 20 has a bellows structure including a pair of bellows portions 21 and 22 and an expansion/contraction restricting portion 23 that is disposed between the pair of bellows portions 21 and 22 and restricts compression of the bellows portions 21 and 22 in an expansion/contraction direction.

With this configuration, compression of the bellows portions 21 and 22 in the expansion/contraction direction is restricted by the expansion/contraction restricting portion 23, and this contributes to softening the contact of the granulated cleaning water GW with a cleaning portion.

A second embodiment of the present invention is described. In the following description, the same components as in the first embodiment are designated by the same reference signs, and the whole or a part of descriptions thereof is omitted.

Figure 7A:
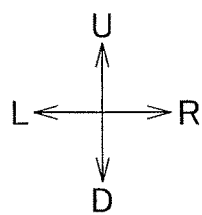
FIG. 7(a) is a front view and FIG. 7(b) is a sectional front view, showing a sealed state of a portable bidet according to a second embodiment of the present invention.
Figure 7A:
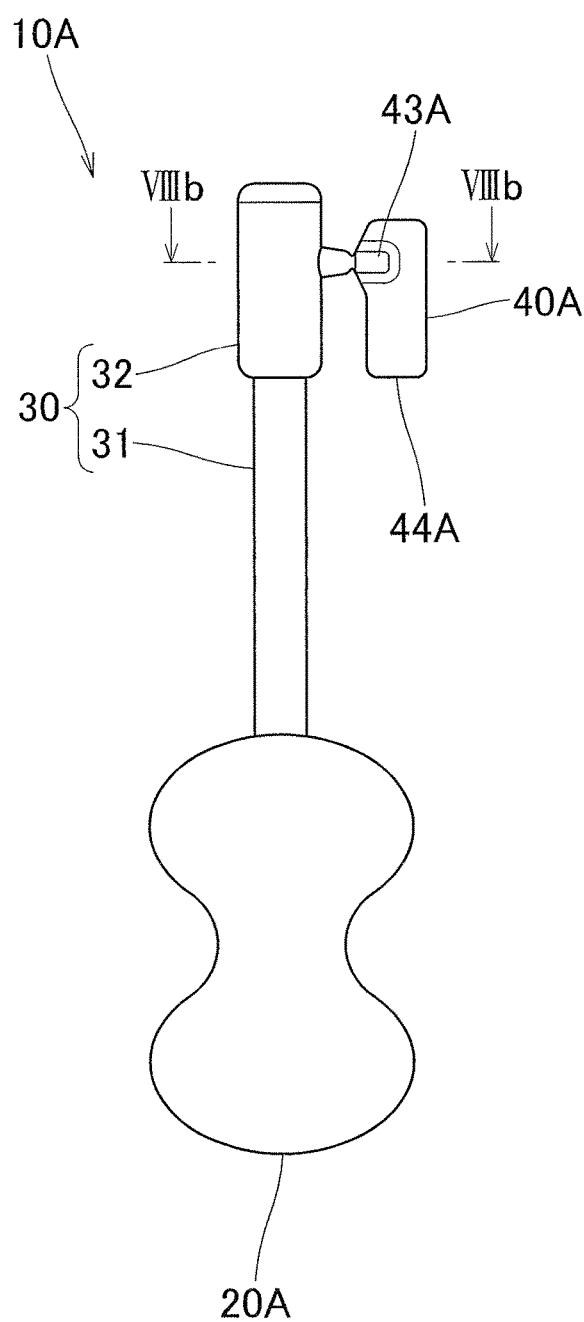
Figure 7B:
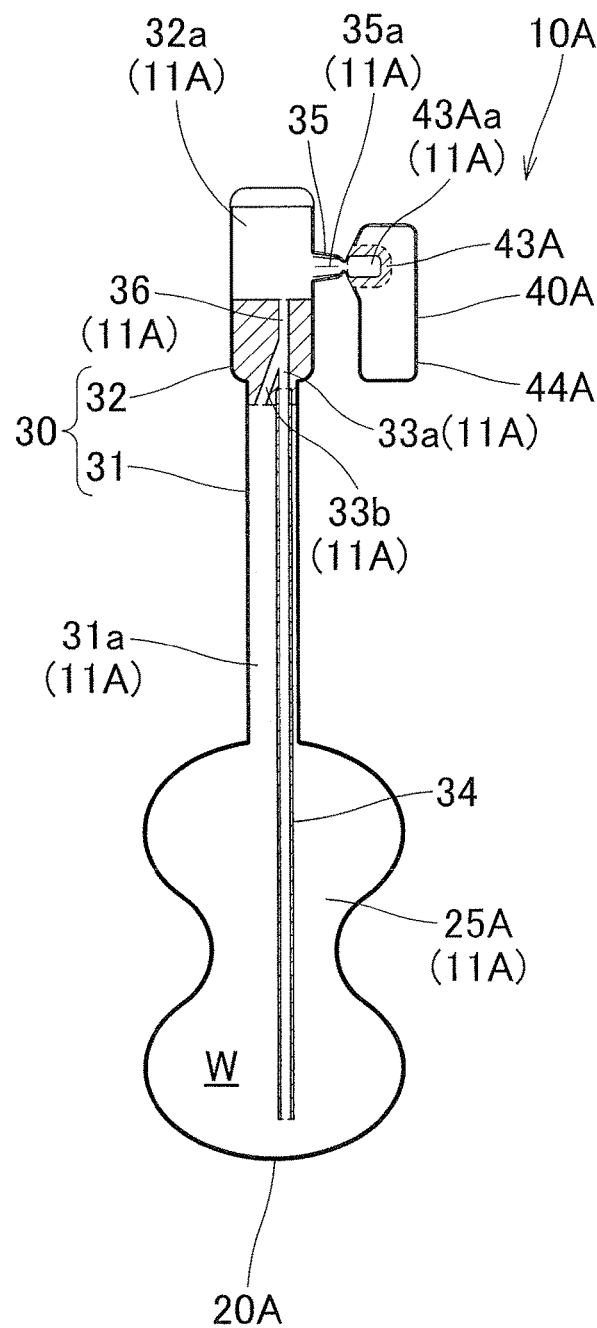
Figure 8A:
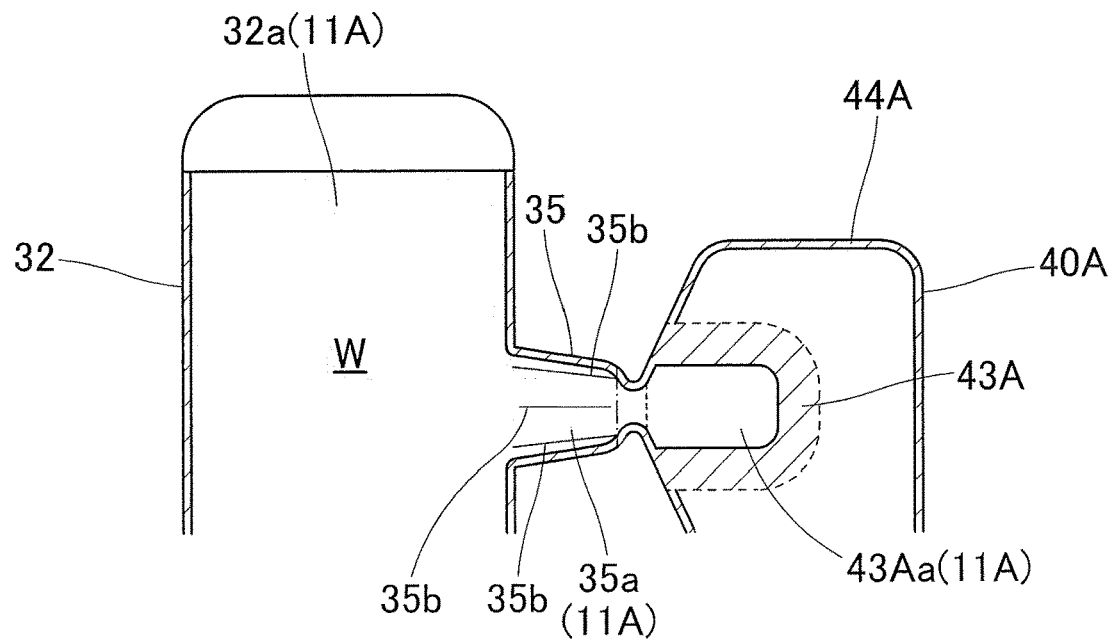
FIG. 8(a) is a partially enlarged sectional view of FIG. 7(b)
Figure 8B:
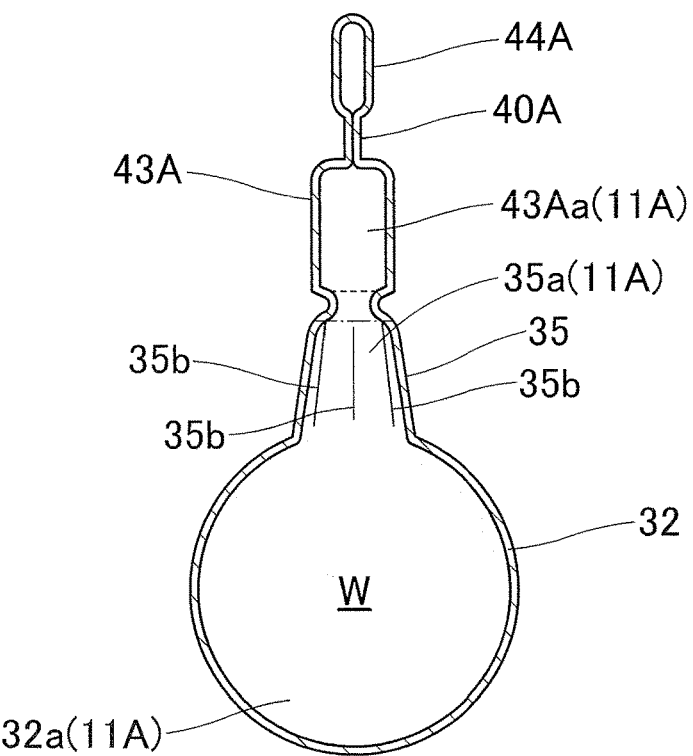
FIG. 8(b) is a sectional view taken in the direction of arrows along line VIIIb-VIIIb in FIG. 7(a).
Figure 9A:
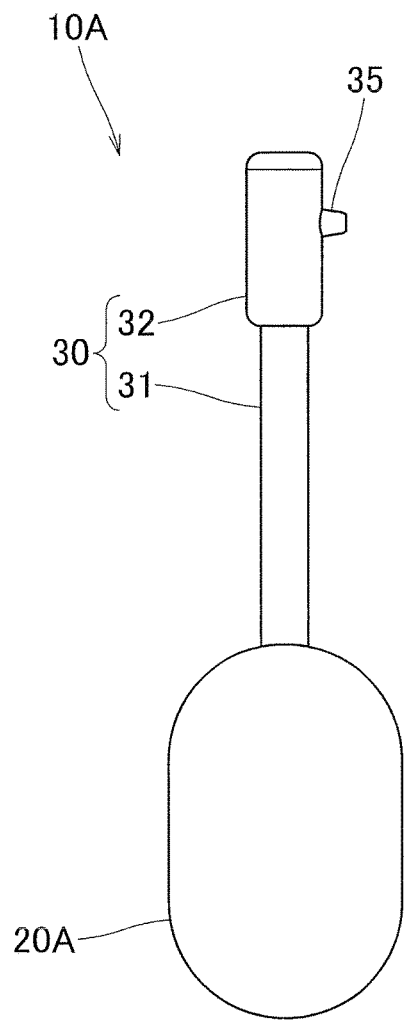
FIG. 9(a) is a front view.
Figure 9B:
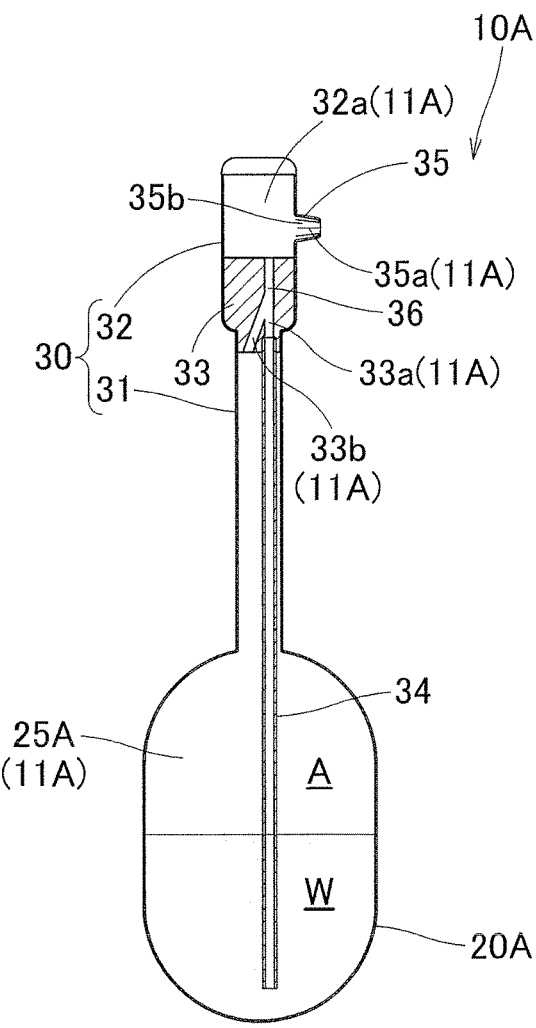
FIG. 9(b) is a sectional front view.
Figure 9C:
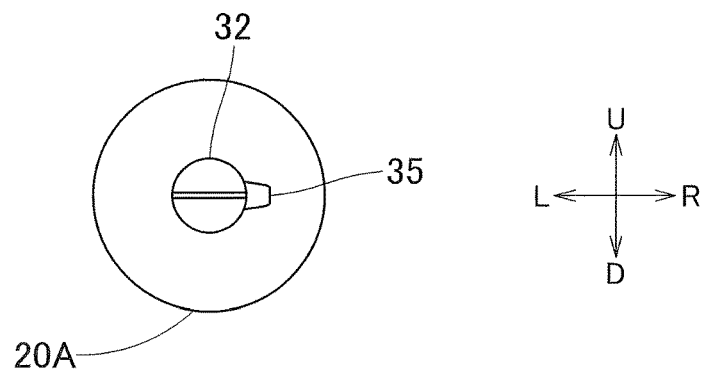
FIG. 9(c) is a plan view, showing an opened state of the portable bidet according to the second embodiment of the present invention.

In the portable bidet 10A, as shown in FIG. 7 to FIG. 9, a tank portion 20A is formed to have a hollow oval spherical interior, and is made to be compression-deformable and restorable to its original shape. In a sealed state, the tank portion assumes a substantially gourd shape whose central portion in an up-down direction is narrowed.

In the present embodiment, as shown in FIG. 8(a) and FIG. 8(b), the flow regulation portions 35b are formed by pinching circumferential wall portions of the nozzle 35 by welding with an injection molding machine or the like into mountain shapes with obtuse apex portions as viewed in the left-right direction, and ridge lines of the mountains are substantially along generating lines of the nozzle 35. In an opened state, the shape of the jetting orifice 35c assumes a substantially cross shape as viewed from a side surface (refer to FIG. 5(a)).

As shown in FIG. 7 and FIG. 8, the sealing portion 40A includes a storing chamber forming portion 43A and a holding margin portion 44A, and is provided continuously to the nozzle 35.

The storing chamber forming portion 43A is formed into a circular cylindrical shape whose right side is blocked, and a space portion inside it is formed as a sealing portion storing chamber 43Aa that communicates with the mixed fluid passage 35a of the nozzle 35 and can be filled with the cleaning water W.

The holding margin portion 44A is formed so as to be hollow inside by being joined together only at outer peripheral edge portions.

The sealing portion 40A changes the portable bidet 10A from a sealed state into an opened state by separating from the nozzle 35 in the state where the portable bidet 10A is sealed.

In the present embodiment, in a state where the portable bidet 10A is sealed, an internal space portion formed by the tank storing chamber 25A of the tank portion 20A, the neck portion storing chamber 31a and the chamber 32a of the jet tube portion 30, the air passage 33a and the cleaning water passage 33b of the solid portion 33, the junction portion 36 of the air passage 33a and the cleaning water passage 33b, the mixed fluid passage 35a of the nozzle 35, and the sealing portion storing chamber 43Aa communicating with each other, is provided as a storing chamber 11A in which the cleaning water W is filled.

This configuration also brings about the same operation and effect as those of the portable bidet 10.

A third embodiment of the present invention is described. In the following description, the same components as in the first embodiment are designated by the same reference signs, and the whole or a part of descriptions thereof is omitted.

Figure 10A:
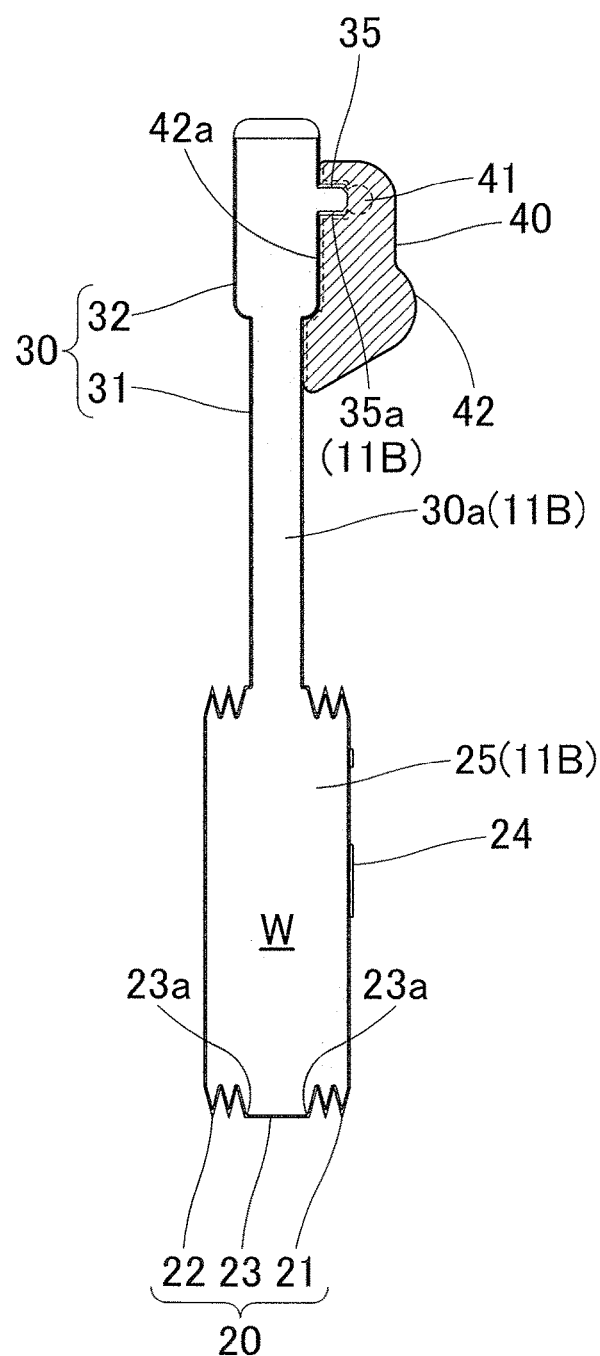
FIG. 10(a) is a sectional front view showing a sealed state and FIG. 10(b) is a sectional front view showing an opened state of a portable bidet according to a third embodiment of the present invention.
Figure 10B:
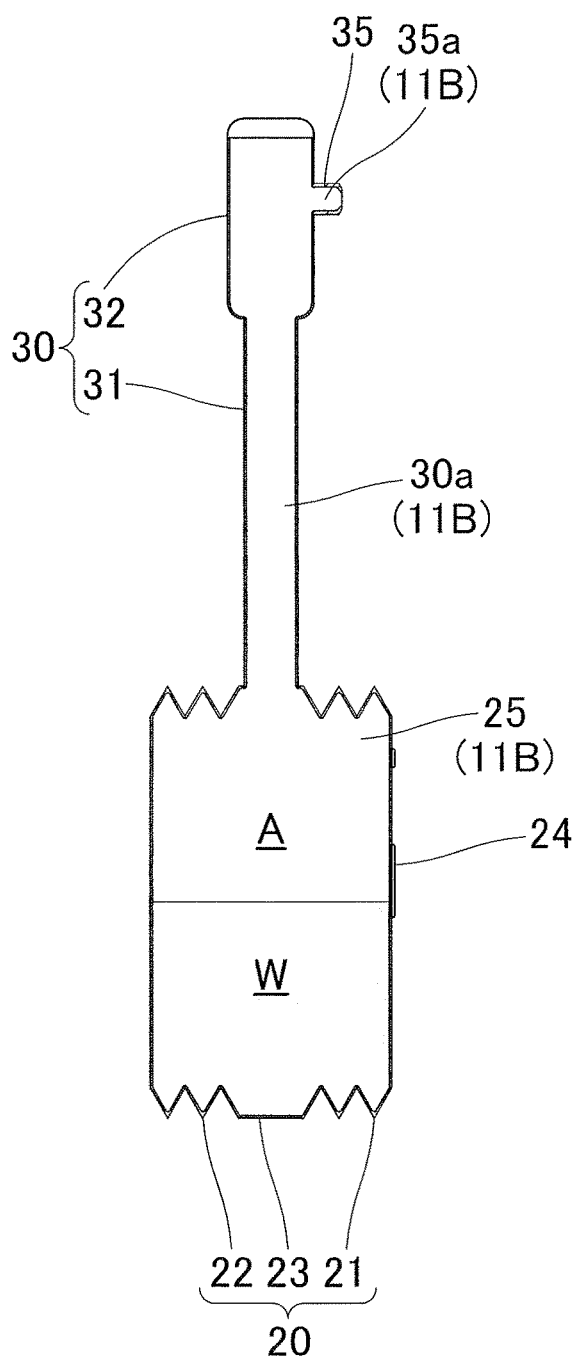

In the portable bidet 10B, as shown in FIG. 10, the jet tube portion 30 is not provided with the solid portion 33, the air distribution tube 34, the air passage 33a, and the cleaning water passage 33b, and the neck portion 31 and the head portion 32 of the jet tube portion 30 are formed to be hollow and have a jet tube storing chamber 30a, and the jet tube storing chamber 30a constitutes a part of a storing chamber 11B for the cleaning water W. Also by this configuration, the quality of the cleaning water W can be maintained.

Hereinafter, a fourth embodiment of the present invention is described based on the drawings. In the present embodiment, as a portable container, a disposable portable bidet 100 capable of cleaning the buttocks is described. As shown in FIG. 12 to FIG. 14, the portable bidet 100 is made of polyethylene, and includes a tank portion 20C, a cylindrical portion 30C, a sealing portion 40C, and a passage forming member 50C.

As shown in FIG. 12 and FIG. 13, the tank portion 20C has a hollow bellows structure that includes a pair of bellows portions 21C and 22C and an expansion/contraction restricting portion 23C that is disposed between the pair of bellows portions 21C and 22C and restricts compression of the bellows portions 21C and 22C in an expansion/contraction direction, and can store cleaning water W (pure water, corresponding to a liquid in claims) as a fluid inside, and is formed to be compression-deformable and restorable to its original shape in the left-right direction (expansion/contraction direction).

In the present embodiment, the bellows of the bellows portion 21C has one mountain fold portion, and the bellows of the bellows portion 22C has three mountain fold portions.

On a left side wall of the bellows portion 22C, as shown in FIG. 12 and FIG. 13, a projection portion 24C annularly projecting leftward is disposed. The projection portion 24C projects in the same direction as a discharging direction of the nozzle 35C described below so that, at the time of use, by touching the projection portion 24C by hand, a user can feel a discharging direction of the cleaning water W without viewing it directly.

The expansion/contraction restricting portion 23C is formed into a cylindrical shape that has a substantially U-shaped lower side and a substantially semicircular arc-shaped upper side as viewed in the left-right direction and is opened in the left-right direction. As can be referred to in FIG. 15, when the bellows portions 21C and 22C are compressed, opening edge portions 23Ca and 23Ca in the left-right direction of the expansion/contraction restricting portion 23C come into contact with the bellows portions 21C and 22C to restrict excessive compression of the bellows portions 21C and 22C in the left-right direction (expansion/contraction direction).

A space portion inside the tank portion 20C is provided as a tank storing chamber 25C constituting a part of the storing chamber 11 in which the cleaning water W is stored.

The cylindrical portion 30C includes, as shown in FIG. 12 and FIG. 13, a neck portion 31C and a head portion 32C, and is connected to the tank portion 20C and can discharge the cleaning water W.

The neck portion 31C is formed into a circular cylindrical shape. A space portion inside the neck portion 31C is provided as a neck portion storing chamber 31Ca constituting a part of the storing chamber 11C in which the cleaning water W is stored. In the neck portion 31C, by the tank storing chamber 25C and the neck portion storing chamber 31Ca communicating with each other, a lower end of the neck portion 31C is connected to the expansion/contraction restricting portion 23C.

The head portion 32C is formed into a circular cylindrical shape with a larger diameter than the neck portion 31C having a space portion, and an upper end thereof is sandwiched together in the left-right direction so that an upper portion becomes gradually narrower upward as viewed in the front-rear direction.

In the vicinity of a boundary portion between the neck portion 31C and the head portion 32C, a passage forming member 50C is fitted.

The passage forming member 50C includes, as shown in FIGS. 12, 13, and 14, a first fitting portion 51C formed so as to fit to the inside of the head portion 32C, a second fitting portion 52C formed so as to fit to the inside of the neck portion 31C, and a prism portion 53C formed into a long prism shape.

In the passage forming member 50C, an air passage 54Ca through which air A is distributed, and a cleaning water passage 54Cb through which cleaning water W is distributed (corresponding to a liquid passage in claims), are disposed.

The air passage 54Ca is formed to extend along a substantially up-down direction from the prism portion 53C to the second fitting portion 52C.

The cleaning water passage 54Cb is formed to extend to a diagonally upper left side from the vicinity of a boundary between the prism portion 53C and the second fitting portion 52C, and join to the air passage 54Ca in the second fitting portion 52C.

The portion at which the air passage 54Ca and the cleaning water passage 54Cb join together is provided as a junction portion 56C.

The first fitting portion 51C and the second fitting portion 52C demarcate the neck portion 31C and the head portion 32C, and can secure sealability between the first fitting portion 51C and the head portion 32C and between the second fitting portion 520 and the neck portion 31C, and do not hinder distribution of the air A through the air passage 54Ca and the cleaning water W through the cleaning water passage 54Cb.

The prism portion 53C is formed to have an external shape to form a gap with an inner surface of the neck portion 31C and enable the cleaning water W to be distributed through the gap portion, and enter the inside of the tank 20C.

In the present embodiment, the prism portion 53C is set to extend to 95% of an inside dimension of the tank portion 20C in the up-down direction, however, it can be properly set in a range of 80 to 95% of the inside dimension of the tank portion 20C in the up-down direction.

In a space portion of the head portion 32C, a portion surrounded by an upper surface of the passage forming member 50C and an inner surface of the head portion 32C is provided as a chamber 32Ca. In the chamber 32Ca, a mixed fluid MF of the air A and granulated cleaning water GW described below is stirred. The chamber 32Ca constitutes a part of the storing chamber 110 in which the cleaning water W is stored.

On a left side wall of the chamber 32Ca, a nozzle 35C capable of discharging the cleaning water W is disposed. The nozzle 35C is formed into a hollow substantially truncated cone shape including a discharge port 35Cc at the left side and having a mixed fluid passage 35Ca. The mixed fluid passage 35Ca constitutes a part of the storing chamber 11C in which the cleaning water W is stored.

The chamber 32Ca in which the mixed fluid MF is stirred is disposed between the junction portion 56C of the air passage 54Ca and the cleaning water passage 54Cb and the nozzle 350.

As shown in FIG. 12, the sealing portion 40C includes an opening assist portion 41C and a holding margin portion 42C, and is provided continuously to the neck portion 31C, the head portion 32C, and the nozzle 35C.

The opening assist portion 41C is formed into a substantially spherical shape, and in a sealed state, blocks the mixed fluid passage 35Ca of the nozzle 35C, and when opening, the opening assist portion 41C is separated from the nozzle 35C to securely form the discharge port 35Cc.

The holding margin portion 42C is formed into a substantially trapezoidal plate shape. At a boundary of the holding margin portion 42C with the neck portion 31C and the head portion 32C, a thinned portion 42Ca formed to be thinner in thickness than other portions of the holding margin portion 42C is disposed so that the sealing portion 40C is easily separated from the cylindrical portion 30C.

As shown in FIG. 12(b), in a state where the portable bidet 100 is sealed, an internal space portion formed by the tank storing chamber 25C of the tank portion 20C, the neck portion storing chamber 31Ca and the chamber 32Ca of the cylindrical portion 30C, the air passage 54Ca and the cleaning water passage 54Cb of the passage forming member 50C, the junction portion 56C of the air passage 54Ca and the cleaning water passage 54Cb, and the mixed fluid passage 35Cc of the nozzle 35c communicating with each other, is provided as the storing chamber 11C in which the cleaning water W is filled.

Figure 15:
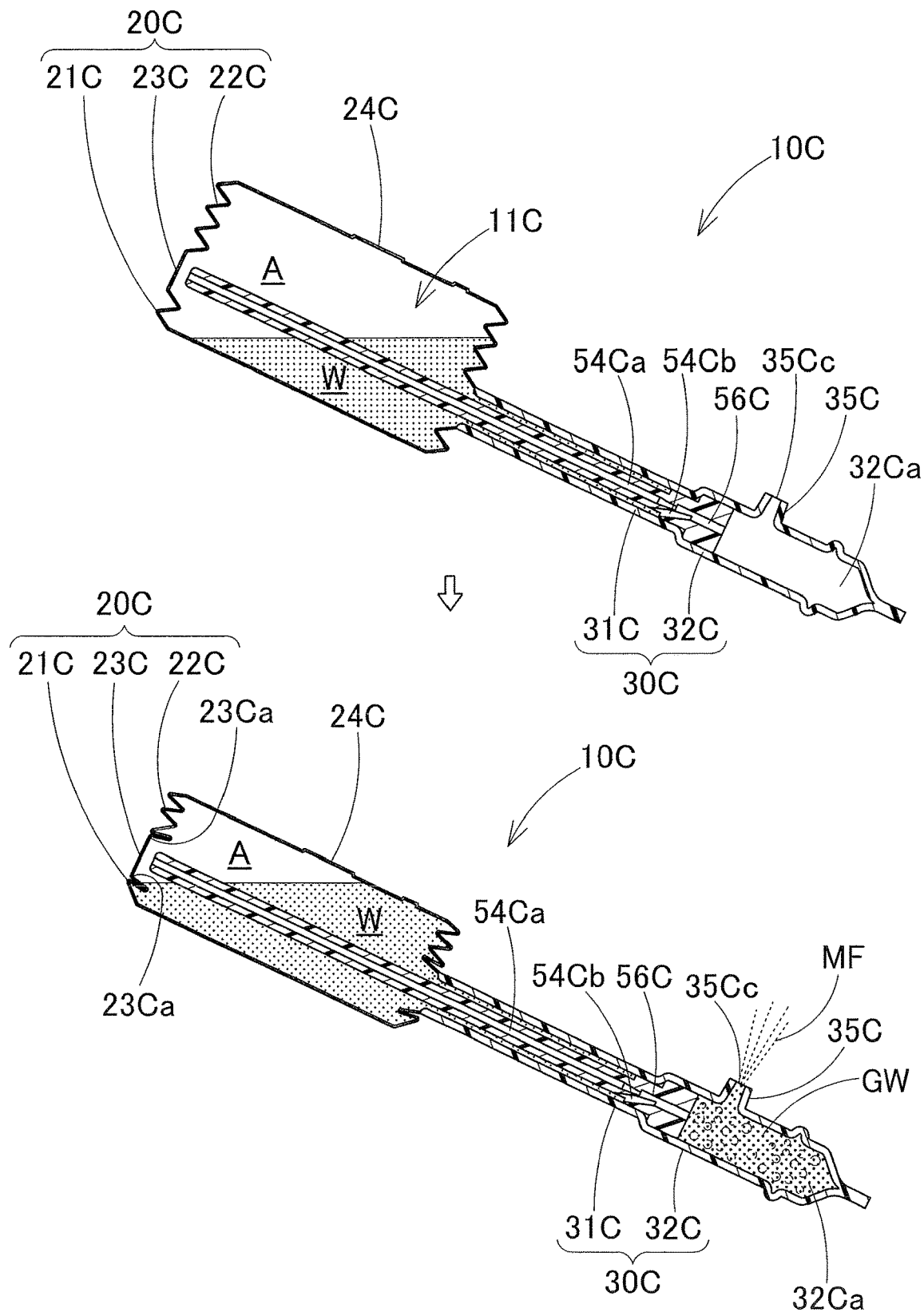
FIG. 15 is an explanatory view showing a usage state of the portable bidet according to the fourth embodiment of the present invention.

In the present embodiment, in the sealed state shown in FIG. 12, a filling amount of the cleaning water W is 12.5 cc when fully filled, and in the usage state shown in FIG. 15, the volume of the storing chamber 11C is set to such an extent that the prism portion 53C is exposed from a liquid level of the cleaning water W.

Next, a usage mode of the portable bidet 10C of the embodiment described above is described. In FIG. 12, the cleaning water W is sealed by the sealing portion 40C, and the tank portion 20C is in a compressed state. From the sealed state shown in FIG. 12, the holding margin portion 42C of the sealing portion 40C is held by hand and torn off from the nozzle 35C and opened. At this time, when the opening assist portion 41C is separated and the discharge port 35Cc is opened, air A enters from the discharge port 35Cc, so that the cleaning water W filled in the storing chamber 11C of the portable bidet 10C does not spurt out. Then, in the state shown in FIG. 13, the tank portion 20C is restored to its original shape.

Then, as shown in FIG. 15, the portable bidet is held by hand so that the cylindrical portion 30C *comes* to the lower side. Since the projection portion 24C projects in the same direction (leftward) as the discharging direction of the nozzle 35C, by touching the projection portion 24C by hand, a user can recognize the discharging direction of the nozzle 35C, and the nozzle 350 is prevented from being turned to the opposite side of a cleaning portion.

Then, in the state shown in FIG. 15, the prism portion 53C is exposed from a liquid level of the cleaning water W, and when the pair of bellows portions 21C and 22C are compressed toward the expansion/contraction restricting portion 230, the tank portion 20C is compressed, and accordingly, air A is distributed through the air passage 54Ca formed in the prism portion 53C, and the cleaning water W is distributed inside the cleaning water passage 54Cb.

Then, when discharging the cleaning water W, the air A distributed through the air passage 54Ca and the cleaning water W distributed through the cleaning water passage 54Cb join together at the junction portion 56C and become a mixed fluid MF of the air A and granulated cleaning water GW.

The mixed fluid MF flows into the chamber 32Ca and is stirred by colliding with an inner wall of the chamber 32Ca, and flows into the nozzle 35C disposed so as to discharge the fluid in a direction different from the flowing-in direction. Then, the mixed fluid MF is discharged to the outside. The cleaning water W constituting the mixed fluid MF is granulated, so that contact thereof with the cleaning portion is softened.

In addition, compression in the expansion/contraction direction of the bellows portions 21C and 22C is restricted in compression by opening edge portions 23Ca and 23Ca of the expansion/contraction restricting portion 23C, and damage to the prism portion 53C is suppressed, and the mixed fluid MF (granulated cleaning water GW) is prevented from being more strongly discharged than necessary.

The portable bidet 10C as a portable container configured as described above includes the tank portion 20C formed to be compression-deformable and restorable to its original shape, the nozzle 35C that is connected to the tank portion 20C and can discharge a fluid, and the sealing portion 400 that is provided continuously to the nozzle 35C and can seal the fluid, and has the storing chamber 11C in which the fluid is stored and which is disposed at least in the tank portion 20C and the nozzle 35C, and in a sealed state where the fluid is sealed by the sealing portion 40C, the fluid is fully filled in the storing chamber 11C while the tank portion 20C is compressed, and in an opened state where sealing by the sealing portion 40C is released, the tank portion 20C is restored to its original shape, and a volume of the storing chamber 11C is expanded as compared with a volume of the storing chamber 11C in the sealed state.

With this configuration, at the time of nonuse, the quality of the cleaning water W is maintained in a sealed state where it does not come into contact with air A, and at the time of use, the state is changed into an opened state and air A is taken into the storing chamber 11C to restore the tank portion 20C to its original shape so that a volume of the storing chamber 11C is expanded as compared with a volume of the storing chamber 11C in the sealed state, making it possible to press the cleaning water W by the taken-in air A, and accordingly, the cleaning water W can be properly discharged to a cleaning portion. When the sealing portion 40C is opened, air A enters from the opened portion and the cleaning water W is pressed into the storing chamber 11C, so that the cleaning water W filled in the storing chamber 11C of the portable bidet 100 does not spurt out, and therefore, the portable bidet can be used without getting hands wet.

In addition, since the tank portion 20C and the nozzle 35C are connected to each other via the cylindrical portion 30C having a cylindrical shape, a hand to compress the tank portion 20C can be kept away from a cleaning portion to which the cleaning water W is discharged, so that the discharged fluid and contamination, etc., can be suppressed from adhering to hands.

In the cylindrical portion 30C, the air passage 54Ca through which air A is distributed, and the cleaning water passage 54Cb through which the cleaning water W is distributed, are disposed, the air passage 54Ca and the cleaning water passage 54Cb are formed to join together, and when discharging the cleaning water W, by compressing the tank portion 20C, the air A distributed through the air passage 54Ca and the cleaning water W distributed through the cleaning water passage 54Cb join together, and a mixed fluid MF of the air A and the granulated cleaning water GW is discharged to the outside.

With this configuration, by discharging the mixed fluid MF of the air A and the granulated cleaning water GW, it is possible to soften the contact of the cleaning water W with a cleaning portion, so that the portable bidet can be used even when the cleaning portion is diseased. By granulating the cleaning water W, the usage of the cleaning water W can be reduced in amount as compared with the case where the cleaning water W in a liquid state is discharged.

To the inside of the cylindrical portion 30C, the passage forming member 50C including the air passage 54Ca and the cleaning water passage 54Cb is fitted.

With this configuration, by the easy operation of fitting the passage forming member 500 to the inside of the cylindrical portion 30C, the air passage 54Ca and the cleaning water passage 54Cb can be provided in the portable bidet 100, so that the number of manufacturing steps and the manufacturing cost can be reduced.

In addition, since the chamber 32Ca in which the mixed fluid MF is stirred is disposed between the junction portion 56C of the air passage 54Ca and the cleaning water passage 54Cb and the nozzle 35C, by stirring the mixed fluid MF, it is possible to soften the contact of the cleaning water W with a cleaning portion as compared with the case where the mixed fluid MF is directly discharged from the junction portion 56C of the air passage 54Ca and the cleaning water passage 54Cb.

In addition, the tank portion 20C has a bellows structure including a pair of bellows portions 21C and 22C and an expansion/contraction restricting portion 23C that is disposed between the pair of bellows portions 21C and 22C and restricts compression of the bellows portions 21C and 22C in an expansion/contraction direction.

With this configuration, compression of the bellows portions 21C and 22C in the expansion/contraction direction is restricted by the expansion/contraction restricting portion 23C, and this contributes to softening of the contact of the granulated cleaning water GW with a cleaning portion.

Figure 17A:
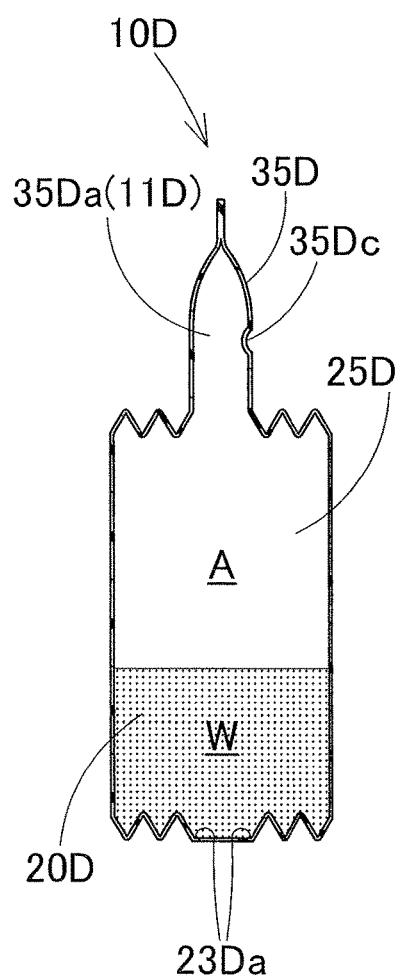
FIG. 17(a) is a sectional front view.
Figure 17B:
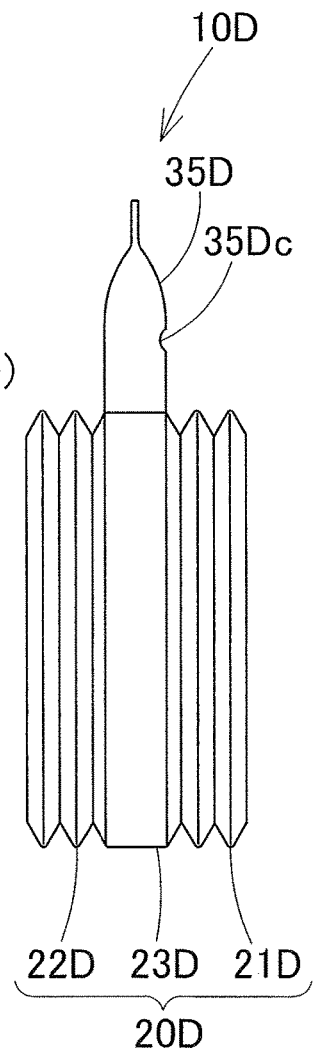
FIG. 17(b) is a front view.
Figure 17C:
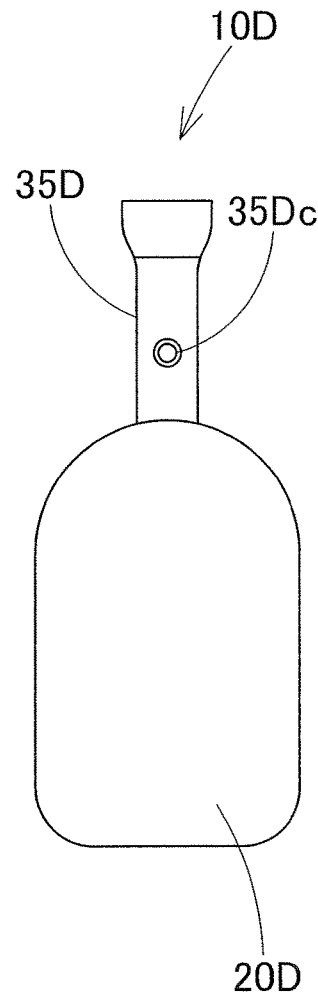
FIG. 17(c) is a right side view, showing an opened state of the portable bidet according to the fifth embodiment of the present invention.

A fifth embodiment of the present invention is described. As shown in FIGS. 16 and 17, a portable bidet 10D is made of polyethylene, and includes a tank portion 20D, a nozzle 35D, and a sealing portion 40D.

The tank portion 20D includes, like the tank portion 20, bellows portions 21D and 22D, an expansion/contraction restricting portion 23D, opening edge portions 23Da, and a tank storing chamber 25D.

The nozzle 35D is formed into a circular cylindrical shape and an upper end thereof is sandwiched together in the left-right direction so that an upper portion becomes gradually narrower upward as viewed in the front-rear direction.

The sealing portion 40D is formed to block only a discharge port 35Dc of the nozzle 35D.

As compared with the fourth embodiment, the cylindrical portion 30C and the passage forming member 50C are not provided, and a storing chamber 11D consists of the tank storing chamber 25D and a nozzle storing chamber 35Da inside the nozzle 35D. In other words, the tank portion 20D and the nozzle 35D are directly connected, and also with this configuration, the quality of the cleaning water W can be maintained.

The portable bidet according to the present invention is not limited to the above-described configurations. That is, various design changes, etc., are possible without departing from the gist of the present invention.

For example, the number of flow regulation portions 35b may be set as appropriate in consideration of their flow regulation effect in such a manner that three flow regulation portions 135b are provided in a nozzle 135 as shown in FIG. 11(a), five flow regulation portions 235b are provided in a nozzle 235 as shown in FIG. 11(b), six flow regulation portions 335b are provided in a nozzle 335 as shown in FIG. 11(c), and two substantially crescent-shaped flow regulation portions 435b are provided in a nozzle 435 as shown in FIG. 11(d).

As a material of the portable bidets 10, 10A, and 10B as portable containers, polyethylene is used, however, other synthetic resins and elastomers, etc., can be used as long as they are compression-deformable and restorable into original shapes.

In the portable bidet 10A, as a configuration in which the storing chamber forming portion 43A is not provided in the sealing portion 40A, a configuration in which the storing chamber 11A in which the cleaning water W is stored is not provided on the sealing portion 40 side can also be adopted.

The number of mountain fold portions of the bellows of each of the bellows portion 21 and 22 can be changed to one or three or more as appropriate.

The fluid can be changed to, besides pure water, oil and fat, water with an added preservative, paint, lotion, and other liquids, gaseous bodies, and gas, etc., as appropriate depending on the intended use (cleaning, application, etc.). In other words, a portable container may be a cleaning container, an applying container, etc., depending on the intended use.

When the air distribution tube 34 can be exposed from the liquid level of the cleaning water W as a fluid as shown in FIG. 6, in an opened state, the volumes of the storing chambers 11 and 11A and the filling amounts of the cleaning water W can be set as appropriate.

In the portable bidet 10C and the portable bidet 10D, it is also possible to cause these portable bidets to accurately discharge granulated cleaning water GW to a cleaning portion by applying the flow regulation portions 35b shown in FIG. 5(a) and FIG. 5(b), or the flow regulation portions 135b, the flow regulation portions 235b, the flow regulation portions 335b, or the flow regulation portions 435b shown in FIG. 11(a), 11(b), 11(c), or 11(d).

In the portable bidet 100 and the portable bidet 10D, it is also possible to provide a storing chamber in which the cleaning water W is stored in the sealing portion 40C or the sealing portion 40D.

REFERENCE SIGNS LIST

10 Portable bidet
10A Portable bidet
10B Portable bidet
10C Portable bidet
10D Portable bidet
11 Storing chamber
11A Storing chamber
11B Storing chamber
11C Storing chamber
11D Storing chamber
20 Tank portion
21 Bellows portion
22 Bellows portion
23 Expansion/contraction restricting portion
23a Opening edge portion
20A Tank portion
20C Tank portion
21C Bellows portion
22C Bellows portion
23C Expansion/contraction restricting portion
23Ca Opening edge portion
20D Tank portion
21D Bellows portion
22D Bellows portion
23D Expansion/contraction restricting portion
23Da Opening edge portion
30 Jet tube portion
32a Chamber
33a Air passage
33b Cleaning water passage
35 Nozzle
35b Flow regulation portion
Junction portion
30C Cylindrical portion
32Ca Chamber
35C Nozzle
35D Nozzle
35Ca Nozzle storing chamber
35Dc Discharge port
135 Nozzle
135b Flow regulation portion
235 Nozzle
235b Flow regulation portion
335 Nozzle
335b Flow regulation portion
435 Nozzle
435b Flow regulation portion 40 Sealing portion
40A Sealing portion
40C Sealing portion
40D Sealing portion
50C Passage forming member
54Ca Air passage
54Cb Cleaning water passage
56C Junction portion
A Air
MF Mixed fluid
W Cleaning water
GW Granulated cleaning water

The invention claimed is:

1. A disposable portable container capable of cleaning the buttocks comprising: a tank portion formed to be compression-deformable and restorable to its original shape; a nozzle that is connected to the tank portion and can discharge a liquid; a cylindrical portion having a cylindrical shape connecting the tank portion and the nozzle; and a sealing portion that is provided continuously to the nozzle and can seal the liquid, and having a storing chamber in which the liquid is stored, disposed at least in the tank portion and the nozzle, wherein in a sealed state where the liquid is sealed by the sealing portion, the liquid is fully filled in the storing chamber in a state where the tank portion is compressed, and in an opened state where sealing by the sealing portion is released, the tank portion is restored to its original shape, and a volume of the storing chamber is expanded as compared with a volume of the storing chamber in the sealed state, a passage forming member having an air passage through which air is distributed and a liquid passage through which the liquid is distributed is fitted to the inside of the cylindrical portion, the air passage and the liquid passage are formed to join together, a chamber in which a mixed fluid is stirred is disposed between a junction portion of the air passage and the liquid passage and the nozzle, a portion surrounded by said passage forming member and said cylindrical portion is provided as a chamber, and when discharging the liquid, by compressing the tank portion, the air distributed through the air passage and the liquid distributed through the liquid passage join together, and the mixed fluid of the air and the liquid granulated is discharged to the outside.

* * * * *